(12) United States Patent
Abderrahim et al.

(10) Patent No.: US 8,105,816 B2
(45) Date of Patent: Jan. 31, 2012

(54) NUCLEIC ACID MOLECULES ENCODING BANK1 SPLICE VARIANTS

(75) Inventors: Hadi Abderrahim, Divonne les Bains (FR); Sergei V. Kozyrev, Uppsala (SE)

(73) Assignee: Merck Serono S. A., Coinsins, Vaud (CH)

( * ) Notice: Subject to any disclaimer, the term of this patent is extended or adjusted under 35 U.S.C. 154(b) by 0 days.

(21) Appl. No.: 12/738,418

(22) PCT Filed: Nov. 21, 2008

(86) PCT No.: PCT/EP2008/065980
§ 371 (c)(1),
(2), (4) Date: Apr. 16, 2010

(87) PCT Pub. No.: WO2009/068481
PCT Pub. Date: Jun. 4, 2009

(65) Prior Publication Data
US 2010/0260746 A1    Oct. 14, 2010

Related U.S. Application Data

(60) Provisional application No. 61/004,480, filed on Nov. 28, 2007.

(30) Foreign Application Priority Data

Nov. 26, 2007 (EP) ...................................... 07121538

(51) Int. Cl.
*C12N 15/09* (2006.01)
*C12N 15/12* (2006.01)
*C12N 5/10* (2006.01)
*C07K 14/435* (2006.01)
*C07K 14/47* (2006.01)

(52) U.S. Cl. ................. 435/252.3; 435/69.1; 435/320.1; 435/325; 530/350

(58) Field of Classification Search ........................ None
See application file for complete search history.

(56) References Cited

U.S. PATENT DOCUMENTS
2007/0072178 A1* 3/2007 Haferlach et al. ................. 435/6
2007/0213939 A1   9/2007 Liew et al.

OTHER PUBLICATIONS

Yu et al. (2003). GenBank Accession No. AY178734.*
Anolik, J. et al. "B Cell Depletion Therapy in Systemic Lupus Erythematosus" *Current Rheumatology Reports*, 2003, pp. 350-356, vol. 5.
Burge, C. B. et al. "Splicing of Precursors to mRNAs by the Spliceosomes" *The RNA World*, Second Edition, 1999, pp. 525-560, Cold Spring Harbor Laboratory Press Cold Spring Harbor, New York.
Cook, S. D. "Advancing treatment with interferon beta-1b (Betaferon/Betaseron) in the next decard: Thinking beyond the standard dose" *J. Neurol.*, 2003, pp. 15-20, vol. 250, Suppl 4.
Dudbridge, F. "Pedigree Disequilibrium Tests for Multilocus Haplotypes" *Genetic Epidemiology*, 2003, pp. 115-121, vol. 25.
Forner, K. et al. "Universal False Discovery Rate Estimation Methodology for Genome-Wide Association Studies" *Hum. Hered.*, 2008, pp. 183-194, vol. 65.
Huck, S. et al. "Expression of B Cell Receptor-Associated Signaling Molecules in Human Lupus" *Autoimmunity*, 2001, pp. 213-224, vol. 33.
Lam, X. M. et al. "The Effect of Benzyl Alcohol on Recombinant Human Interferon-γ" *Pharmaceutical Research*, 1997, pp. 725-729, vol. 14, No. 6, XP-002303727.
Liossis, S. C. et al. "B-Cell Kinase Lyn Deficiency in Patients With Systemic Lupus Erythemastosus" *Journal of Investigative Medicine*, Mar. 2001, pp. 157-165, vol. 49, No. 2.
Aiba, Y. et al. "Bank Negatively Regulates Akt Activation and Subsequent B Cell Responses" *Immunity*, Mar. 2006, pp. 259-268, vol. 24.
Blom, N. et al. "Sequence and Structure-based Prediction of Eukaryotic Protein Phosphorylation Sites" *J. Mol. Biol.*, 1999, pp. 1351-1362, vol. 294.
Cornall, R. J. et al. "Polygenic Autoimmune Traits: Lyn, CD22, and SHP-1 Are Limiting Elements of a Biochemical Pathway Regulating BCR Signaling and Selection" *Immunity*, Apr. 1998, pp. 497-508, vol. 8.
Flores, F.-B. et al. "Decreased Lyn Expression and Translocation to Lipid Raft Signaling Domains in B Lymphocytes From Patients with Systemic Lupus Erythmatosus" *Arthritis & Rheumatism*, Dec. 2005, pp. 3955-3965, vol. 52, No. 12.
Freeman, W. M et al. "Proteomics for Protein Expression Profiling in Neuroscience" *Neurochemical Research*, Jun. 2004, pp. 1065-1081, vol. 29, No. 6.
Guedj, M. et al. "A Fast, Unbiased and Exact Allelic Test for Case-Control Association Studies" *Human Heredity*, 2006, pp. 210-221, vol. 61.
Gut, I. G. "DNA Analysis by MALDI-TOF Mass Spectrometry" *Human Mutation*, 2004, pp. 437-441, vol. 23.
Hibbs, M. L. et al. "Sustained Activation of Lyn Tyrosine Kinase In Vivo Leads to Autoimmunity" *J. Exp. Med.*, Dec. 16, 2002, pp. 1593-1604, vol. 196, No. 12.
Jordan, M. S. et al. "Adaptors as central mediators of signal transduction in immune cells" *Nature Immunology*, Feb. 2003, pp. 110-116, vol. 4, No. 2.
Kozyrev, S. V. et al. "Functional variants in the B-cell gene *BANK1* are associated with systemic lupus erythematosus" *Nature Genetics*, Feb. 2008, pp. 211-216, vol. 40, No. 2.
Kozyrev, S. V. et al. "Structural Insertion/Deletion Variation in IRF5 Is Associated With a Risk Haplotype and Defines the Precise IRF5 Isoforms Expressed in Systemic Lupus Erythematosus" *Arthritis & Rheumatism*, Apr. 2007, pp. 1234-1241, vol. 56, No. 4.
Kurosaki, T. "Regulation of B-Cell Signal Transduction by Adaptor Proteins" *Nature*, May 2002, pp. 354-363, vol. 2.
Liossis, S.-N. C. "B Cells from Patients with Systemic Lupus Erythematosus Display Abnormal Antigen Receptor-mediated Early Signal Transduction Events" *J. Clin. Invest.*, Dec. 1996, pp. 2549-2557, vol. 98, No. 11.
Mohler, P. J. "Ankyrin-B mutation causes type 4 long-QT cardiac arrhythmia and sudden cardiac death" *Nature*, Feb. 6, 2003, pp. 634-639, vol. 421.

(Continued)

*Primary Examiner* — Christine J Saoud
*Assistant Examiner* — Jon M Lockard
(74) *Attorney, Agent, or Firm* — Saliwanchik, Lloyd & Eisenschenk

(57) ABSTRACT

The present invention relates to a new splice variant of BANK1, the use of SNPs in BANK1 for diagnostics and the use of antagonists to modulate BANK1 and/or the BANK1 pathway.

19 Claims, 7 Drawing Sheets

OTHER PUBLICATIONS

Figure 1A:
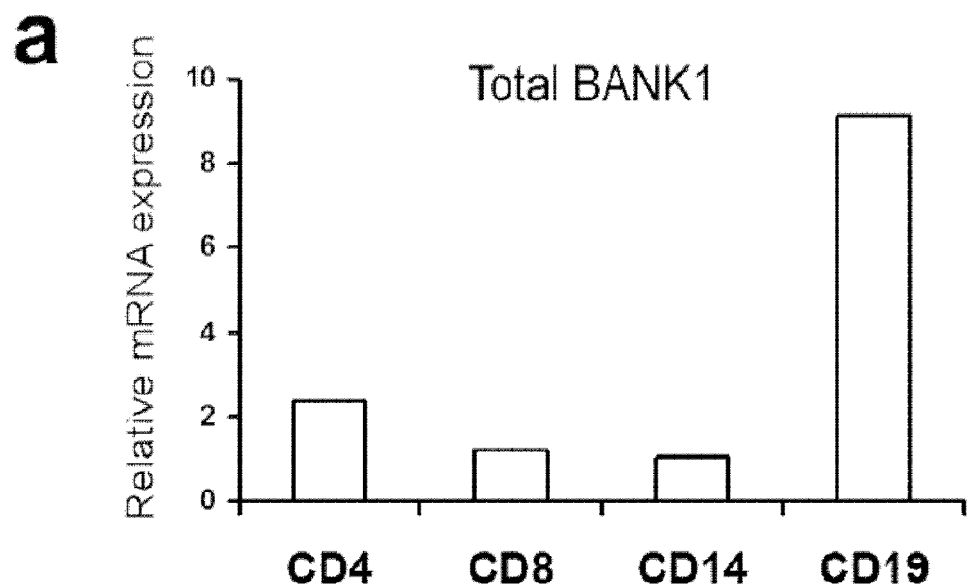

Okada, T. et al. "BCAP: The Tyrosine Kinase Substrate that Connects B Cell Receptor to Phosphoinositide 3-Kinase Activation" *Immunity*, Dec. 2000, pp. 817-827, vol. 13.

Patterson, R. L. et al. "Inositol 1,4,5-Trisphosphate Receptors as Signal Integrators" *Annu. Rev. Biochem.*, 2004, pp. 437-465, vol. 73.

Sherer, Y. et al. "Autoantibody Explosion in Systemic Lupus Erythematosus: More than 100 Different Antibodies Found in SLE Patients" *Seminars in Arthritis and Rheumatism*, 2004, pp. 501-537, vol. 34.

Shi, M. M. "Enabling Large-Scale Pharmacogenic Studies by High-Throughput Mutation Detection and Genotyping Technologies" *Clinical Chemistry*, 2001, pp. 164-172, vol. 47, No. 2.

Stephens, M. et al. "A New Statistical Method for Haplotype Reconstruction" *Am. J. Hum, Genet.*, 2001, pp. 979-989, vol. 68.

Stephens, M. et al. "A Comparison of Bayesian Methods for Haplotype Reconstruction from Population Genotype Data" *Am. J. Hum. Genet.*, 2003, pp. 1162-1169, vol. 73.

Tan, E. M. et al. "The 1982 Revised Criteria for the Classification of Systemic Lupus Erythematosus" *Arthritis & Rheumatism*, Nov. 1982, pp. 1271-1277, vol. 25, No. 11.

Yokoyama, K. et al. "BANK regulates BCR-induced calcium mobilization by promoting tyrosine phosphorylation of $IP_3$ receptor" *The EMBO Journal*, 2002, pp. 83-92, vol. 21, Nos. 1 & 2.

Zhu, H. et al. "Protein chip technology" *Current Opinion in Chemical Biology*, 2003, pp. 55-63, vol. 7.

Database DBSNP, Accession No. rs3733197, Sep. 28, 2005, XP-002478896, pp. 1-2.

Database DBSNP, Accession No. rs10516487, Aug. 10, 2004, XP-002478894, pp. 1-2.

Database EMBL, Accession No. AY178734, "*Mus musculus* AVIEF mRNA, partial cds" Mar. 3, 2003, XP-002478893, pp. 1-2.

Database DBSNP, Accession No. rs17266594, Aug. 10, 2004, XP-002478895, pp. 1-2.

Written Opinion in International Application No. PCT/EP2008/065980, Mar. 6, 2009, pp. 1-10.

* cited by examiner

Fig. 2c

SEQUENCE LISTING

```
<160> NUMBER OF SEQ ID NOS: 24

<210> SEQ ID NO 1
<211> LENGTH: 1984
<212> TYPE: DNA
<213> ORGANISM: Homo sapiens

<400> SEQUENCE: 1
tcaaccgcca caatgctgcc agcagcgcca ggcaaggggc ttgggagccc ggaccccgcc      60
ccctgcggcc cagcgccccc agattctgaa gactactttg aggtcaacat tccaacagac     120
ctacgagcaa acattctgg ggaaataagt gagagaaagg aaattgaaga actatcagaa      180
gcttcaagaa acaccatacc actagcagtg gtgcttccca ctgaaattcc atgtgagaat     240
cctggtgaaa tattcataat tttgagagat gaagtaattg gtgatactgt agaggttgaa     300
tttacatcaa gtaataagcg cattagaaca cggccagccc tttggaataa gaaagtctgg     360
tgcatgaaag ctttagagtt tcctgctggt tcagtccatg tcaatgtcta ctgtgatgga     420
atcgttaaag ctacaaccaa aattaagtac tacccaacag caaaggcaaa ggaatgccta     480
ttcagaatgg cagattcagg agagagtttg tgccagaata gcattgaaga acttgatggt     540
gtccttacat ccatattcaa acatgagata ccatattatg agttccagtc tctttcaaact    600 gaaatttgtt ctcaaaacaa atatactcat ttcaaagaac ttccaactct tctccactgt    660
gcagcaaaat ttggcttaaa gaacctggct attcatttgc ttcaatgttc aggagcaacc    720
tgggcatcta agatgaaaaa tatggagggt tcagaccccg cacatattgc tgaaaggcat    780
ggtcacaaag aactcaagaa aatcttcgaa gactttttcaa tccaagaaat tgacataaat    840
aatgagcaag aaaatgatta tgaagaggat attgcctcat tttccacata tattccttcc    900
acacagaacc cagcatttca tcatgaaagc aggaagacat acgggcagag tgcagatgga    960
gctgaggcaa atgaaatgga aggggaagga aaacagaatg gatcaggcat ggagaccaaa   1020
cacagcccac tagaggttgg cagtgagagt tctgaagacc agtatgatga cttgtatgtg   1080
ttcattcctg gtgctgatcc agaaaataat tcacaagagc cactcatgag cagcagacct   1140 cctctcccccc cgccgcgacc tgtagctaat gccttccaac tggaaagacc tcacttcacc   1200
ttaccaggga caatggtgga aggccaaatg gaaagaagtc aaaactgggg tcatcctggt   1260
gttagacaag aaacaggaga tgaacccaaa ggagaaaaag agaagaaaga agaggaaaaa   1320
gagcaggagg aggaagaaga cccatatact tttgctgaga ttgatgacag tgaatatgac   1380
atgatattgg ccaatctgag tataaagaaa aaaactggga gtcggtcttt cattataaat   1440
agacctcctg cccccacacc ccgacccaca agtataccct caaaagagga aactacacct   1500
tacatagctc aagtgtttca acaaaagaca gccagaagac aatctgatga tgacaagttc   1560
cgtggtcttc ctaagaaaca agacagagct cggatagaga gtccagcctt ttctactctc   1620
aggggctgtc taactgatgg tcaggaagaa ctcatcctcc tgcaggagaa agtaaagaat   1680
gggaaaatgt ctatggatga agctctggag aaatttaaac actggcagat gggaaaaagt   1740
ggcctggaaa tgattcagca ggagaaatta cgacaactac gagactgcat tattgggaaa   1800
```

```
aggccagaag aagaaaatgt ctataataaa ctcaccattg tgcaccatcc aggtggtaag    1860
gaaactgccc acaatgaaaa taagtttat aatgtacact tcagcaataa gcttcctgct    1920 cgacccaag ttgaaaagga atttggtttc tgttgcaaga aagatcatta aagaaggtta    1980
ttat                                                                1984

<210> SEQ ID NO 2
<211> LENGTH: 652
<212> TYPE: PRT
<213> ORGANISM: Homo sapiens

<400> SEQUENCE: 2

Met Leu Pro Ala Ala Pro Gly Lys Gly Leu Gly Ser Pro Asp Pro Ala
1               5                   10                  15

Pro Cys Gly Pro Ala Pro Pro Asp Ser Glu Asp Tyr Phe Glu Val Asn
            20                  25                  30

Ile Pro Thr Asp Leu Arg Ala Lys His Ser Gly Glu Ile Ser Glu Arg
        35                  40                  45

Lys Glu Ile Glu Glu Leu Ser Glu Ala Ser Arg Asn Thr Ile Pro Leu
    50                  55                  60

Ala Val Val Leu Pro Thr Glu Ile Pro Cys Glu Asn Pro Gly Glu Ile
65                  70                  75                  80

Phe Ile Ile Leu Arg Asp Glu Val Ile Gly Asp Thr Val Glu Val Glu
                85                  90                  95

Phe Thr Ser Ser Asn Lys Arg Ile Arg Thr Arg Pro Ala Leu Trp Asn
            100                 105                 110

Lys Lys Val Trp Cys Met Lys Ala Leu Glu Phe Pro Ala Gly Ser Val
        115                 120                 125

His Val Asn Val Tyr Cys Asp Gly Ile Val Lys Ala Thr Thr Lys Ile
    130                 135                 140

Lys Tyr Tyr Pro Thr Ala Lys Ala Lys Glu Cys Leu Phe Arg Met Ala
145                 150                 155                 160

Asp Ser Gly Glu Ser Leu Cys Gln Asn Ser Ile Glu Glu Leu Asp Gly
                165                 170                 175

Val Leu Thr Ser Ile Phe Lys His Glu Ile Pro Tyr Tyr Glu Phe Gln
            180                 185                 190

Ser Leu Gln Thr Glu Ile Cys Ser Gln Asn Lys Tyr Thr His Phe Lys
        195                 200                 205

Glu Leu Pro Thr Leu Leu His Cys Ala Ala Lys Phe Gly Leu Lys Asn
    210                 215                 220

Leu Ala Ile His Leu Leu Gln Cys Ser Gly Ala Thr Trp Ala Ser Lys
225                 230                 235                 240

Met Lys Asn Met Glu Gly Ser Asp Pro Ala His Ile Ala Glu Arg His
                245                 250                 255

Gly His Lys Glu Leu Lys Lys Ile Phe Glu Asp Phe Ser Ile Gln Glu
            260                 265                 270

Ile Asp Ile Asn Asn Glu Gln Glu Asn Asp Tyr Glu Glu Asp Ile Ala
        275                 280                 285

Ser Phe Ser Thr Tyr Ile Pro Ser Thr Gln Pro Ala Phe His His
    290                 295                 300

Glu Ser Arg Lys Thr Tyr Gly Gln Ser Ala Asp Gly Ala Glu Ala Asn
305                 310                 315                 320

Glu Met Glu Gly Glu Gly Lys Gln Asn Gly Ser Gly Met Glu Thr Lys
                325                 330                 335
```

His Ser Pro Leu Glu Val Gly Ser Glu Ser Ser Glu Asp Gln Tyr Asp
            340                 345                 350

Asp Leu Tyr Val Phe Ile Pro Gly Ala Asp Pro Glu Asn Asn Ser Gln
            355                 360                 365

Glu Pro Leu Met Ser Ser Arg Pro Pro Leu Pro Pro Arg Pro Val
370                 375                 380

Ala Asn Ala Phe Gln Leu Glu Arg Pro His Phe Thr Leu Pro Gly Thr
385                 390                 395                 400

Met Val Glu Gly Gln Met Glu Arg Ser Gln Asn Trp Gly His Pro Gly
                405                 410                 415

Val Arg Gln Glu Thr Gly Asp Glu Pro Lys Gly Glu Lys Glu Lys
            420                 425                 430

Glu Glu Glu Lys Glu Gln Glu Glu Glu Asp Pro Tyr Thr Phe Ala
            435                 440                 445

Glu Ile Asp Asp Ser Glu Tyr Asp Met Ile Leu Ala Asn Leu Ser Ile
            450                 455                 460

Lys Lys Lys Thr Gly Ser Arg Ser Phe Ile Ile Asn Arg Pro Pro Ala
465                 470                 475                 480

Pro Thr Pro Arg Pro Thr Ser Ile Pro Pro Lys Glu Glu Thr Thr Pro
            485                 490                 495

Tyr Ile Ala Gln Val Phe Gln Gln Lys Thr Ala Arg Arg Gln Ser Asp
            500                 505                 510

Asp Asp Lys Phe Arg Gly Leu Pro Lys Lys Gln Asp Arg Ala Arg Ile
            515                 520                 525

Glu Ser Pro Ala Phe Ser Thr Leu Arg Gly Cys Leu Thr Asp Gly Gln
            530                 535                 540

Glu Glu Leu Ile Leu Leu Gln Glu Lys Val Lys Asn Gly Lys Met Ser
545                 550                 555                 560

Met Asp Glu Ala Leu Glu Lys Phe Lys His Trp Gln Met Gly Lys Ser
            565                 570                 575

Gly Leu Glu Met Ile Gln Gln Glu Lys Leu Arg Gln Leu Arg Asp Cys
            580                 585                 590

Ile Ile Gly Lys Arg Pro Glu Glu Glu Asn Val Tyr Asn Lys Leu Thr
            595                 600                 605

Ile Val His His Pro Gly Gly Lys Glu Thr Ala His Asn Glu Asn Lys
            610                 615                 620

Phe Tyr Asn Val His Phe Ser Asn Lys Leu Pro Ala Arg Pro Gln Val
625                 630                 635                 640

Glu Lys Glu Phe Gly Phe Cys Cys Lys Lys Asp His
            645                 650

<210> SEQ ID NO 3
<211> LENGTH: 1983
<212> TYPE: DNA
<213> ORGANISM: Pan troglodytes

<400> SEQUENCE: 3
tcaaccgcca caatgctgcc agcagcgcca ggcaagggc ttgggagccc ggacccggcc      60
ccctgcggcc cagcgccccc agattctgaa gactactttg aggtcaacat tccaacagac     120
ctacgagcaa acattctggg gaaataagt gagagaaagg aaattgaaga actatcagaa     180
gcttcaagaa acaccatacc actagcagtg gtgcttccca ctgaaattcc atgtgagaat     240
cctggtgaaa tattcataat tttgagagat gaagtaattg gtgatactgt agaggttgaa     300
tttacatcac gtaataagcg cattagaaca cggccagccc tttggaataa gaaagtctgg     360

```
tgcgtgaaag ctttagagtt tcctgctggt tcagtccatg tcaatgtcta ctgtgatgga    420
atcgttaaag ctacaaccaa aattaagtac tacccaacag caaaggcaaa ggaatgccta    480
ttcagaatgg cagattcaag agagagtttg tgccagaata gcattgaaga acttgatggt    540
gtccttacat ccatattcaa acatgagata ccatattatg agttccaatc tcttcaaact    600
gaaatttgtt ctcaaaacaa atatactcat tcaaagaac ttccaactct tctccactgt     660
gcagcaaaat ttggcttaaa aacctggct attcatttgc ttcaatgttc aggagcaacc    720
tgggcatcta agatgaaaaa tacggagggt tcagaccccg cacatattgc tgaaagacat    780
ggtcacaaag aactcaagaa aatcttcgaa gacttttcaa tccaagaaat tgacataaat    840
aatgagcaag aaaatgatta tgaagaggat attgcctcat tttccacata tattccttcc    900
acacagaacc cagcatttca tcatgaaagc aggaagacat acgggcagag tgcagatgga    960
gctgaggcaa atgaaatgga aggggaagga aaacagaatg gatcaggcat ggagaccaaa   1020
cacagcccac tagaggttgg cagtgagagt tctgaggacc agtatgatga cttgtatgtg   1080
ttcattcctg gtgctgatcc agaaaataat tcacaagagc cactcatgag cagcagacct   1140
cctctccccc cgccgcgacc tgtagctaat gccttccaac tggaaagacc tcacttcacc   1200
ttaccaggga caacggtgga aggccaaatg gaaagaagtc aaaactgggg tgatcctggt   1260
gttagacaag aaacaggaga tgaacccaaa ggagaaaaag agaagaaaga agacgaaaaa   1320
gagcaggagg aggaagaaga cccatatact tttgctgaga ttgatgacag tgaatatgac   1380
atgatattgg ccaatctgag tataaagaaa aaaactggga gtcggtcttt cattataaat   1440
agacctcctg cccccacacc ccgacccaca agtaaacctc caaagagga aactacacct    1500 tacatagctc aagtgtttca acaaaagaca gccagaagac aatctgatga tgacaagttc   1560
cgtggtcttc ctaagaaaca agacagagct cggatagaga gtccagcttt ttctactctc   1620 agggctgtc taactgatgg tcaggaagaa ctcatcctcc tgcaggagaa agtcaagaat    1680
gggaaaatgt ctatggatga agctctggag aaatttaaac actggcagat gggaaaagt    1740 ggcctggaaa tgattcagca ggagaaatta cggcaactac gagactgcat tattgggaaa   1800
aggccagaag aagaaaatgt ctataataaa ctcaccattg tgcaccatcc aggtggtaag   1860
gaaactgccc acaatgaaaa taagttttat aatgtacact tcagcaataa gcttcctgct   1920
cgaccccaag ttgaaaagga atttggtttc tgttgcaaga agatcatta aaggaggtta   1980 tta                                                                 1983
```

<210> SEQ ID NO 4
<211> LENGTH: 652
<212> TYPE: PRT
<213> ORGANISM: Pan troglodytes

<400> SEQUENCE: 4

```
Met Leu Pro Ala Pro Gly Lys Gly Leu Gly Ser Pro Asp Pro Ala
1               5                   10                  15

Pro Cys Gly Pro Ala Pro Pro Asp Ser Glu Asp Tyr Phe Glu Val Asn
                20                  25                  30

Ile Pro Thr Asp Leu Arg Ala Lys His Ser Gly Glu Ile Ser Glu Arg
                35                  40                  45

Lys Glu Ile Glu Glu Leu Ser Glu Ala Ser Arg Asn Thr Ile Pro Leu
            50                  55                  60

Ala Val Val Leu Pro Thr Glu Ile Pro Cys Glu Asn Pro Gly Glu Ile
65                  70                  75                  80

Phe Ile Ile Leu Arg Asp Glu Val Ile Gly Asp Thr Val Glu Val Glu
```

-continued

```
                85                  90                  95
Phe Thr Ser Arg Asn Lys Arg Ile Arg Thr Arg Pro Ala Leu Trp Asn
            100                 105                 110
Lys Lys Val Trp Cys Val Lys Ala Leu Glu Phe Pro Ala Gly Ser Val
        115                 120                 125
His Val Asn Val Tyr Cys Asp Gly Ile Val Lys Ala Thr Thr Lys Ile
    130                 135                 140
Lys Tyr Tyr Pro Thr Ala Lys Ala Lys Glu Cys Leu Phe Arg Met Ala
145                 150                 155                 160
Asp Ser Arg Glu Ser Leu Cys Gln Asn Ser Ile Glu Glu Leu Asp Gly
                165                 170                 175
Val Leu Thr Ser Ile Phe Lys His Glu Ile Pro Tyr Tyr Glu Phe Gln
            180                 185                 190
Ser Leu Gln Thr Glu Ile Cys Ser Gln Asn Lys Tyr Thr His Phe Lys
        195                 200                 205
Glu Leu Pro Thr Leu Leu His Cys Ala Ala Lys Phe Gly Leu Lys Asn
    210                 215                 220
Leu Ala Ile His Leu Leu Gln Cys Ser Gly Ala Thr Trp Ala Ser Lys
225                 230                 235                 240
Met Lys Asn Thr Glu Gly Ser Asp Pro Ala His Ile Ala Glu Arg His
                245                 250                 255
Gly His Lys Glu Leu Lys Lys Ile Phe Glu Asp Phe Ser Ile Gln Glu
            260                 265                 270
Ile Asp Ile Asn Asn Glu Gln Glu Asn Asp Tyr Glu Glu Asp Ile Ala
        275                 280                 285
Ser Phe Ser Thr Tyr Ile Pro Ser Thr Gln Asn Pro Ala Phe His His
    290                 295                 300
Glu Ser Arg Lys Thr Tyr Gly Gln Ser Ala Asp Gly Ala Glu Ala Asn
305                 310                 315                 320
Glu Met Glu Gly Glu Lys Gln Asn Gly Ser Gly Met Glu Thr Lys
                325                 330                 335
His Ser Pro Leu Glu Val Gly Ser Glu Ser Ser Glu Asp Gln Tyr Asp
            340                 345                 350
Asp Leu Tyr Val Phe Ile Pro Gly Ala Asp Pro Glu Asn Asn Ser Gln
        355                 360                 365
Glu Pro Leu Met Ser Ser Arg Pro Pro Leu Pro Pro Arg Pro Val
    370                 375                 380
Ala Asn Ala Phe Gln Leu Glu Arg Pro His Phe Thr Leu Pro Gly Thr
385                 390                 395                 400
Thr Val Glu Gly Gln Met Glu Arg Ser Gln Asn Trp Gly Asp Pro Gly
                405                 410                 415
Val Arg Gln Glu Thr Gly Asp Glu Pro Lys Gly Glu Lys Glu Lys Lys
            420                 425                 430
Glu Asp Glu Lys Glu Gln Glu Glu Glu Asp Pro Tyr Thr Phe Ala
        435                 440                 445
Glu Ile Asp Asp Ser Glu Tyr Asp Met Ile Leu Ala Asn Leu Ser Ile
    450                 455                 460
Lys Lys Lys Thr Gly Ser Arg Ser Phe Ile Ile Asn Arg Pro Pro Ala
465                 470                 475                 480
Pro Thr Pro Arg Pro Thr Ser Lys Pro Pro Lys Glu Glu Thr Thr Pro
                485                 490                 495
Tyr Ile Ala Gln Val Phe Gln Gln Lys Thr Ala Arg Arg Gln Ser Asp
            500                 505                 510
```

```
Asp Asp Lys Phe Arg Gly Leu Pro Lys Lys Gln Asp Arg Ala Arg Ile
            515                 520                 525

Glu Ser Pro Ala Phe Ser Thr Leu Arg Gly Cys Leu Thr Asp Gly Gln
        530                 535                 540

Glu Glu Leu Ile Leu Leu Gln Glu Lys Val Lys Asn Gly Lys Met Ser
545                 550                 555                 560

Met Asp Glu Ala Leu Glu Lys Phe Lys His Trp Gln Met Gly Lys Ser
                565                 570                 575

Gly Leu Glu Met Ile Gln Gln Glu Lys Leu Arg Gln Leu Arg Asp Cys
            580                 585                 590

Ile Ile Gly Lys Arg Pro Glu Glu Glu Asn Val Tyr Asn Lys Leu Thr
        595                 600                 605

Ile Val His His Pro Gly Gly Lys Glu Thr Ala His Asn Glu Asn Lys
    610                 615                 620

Phe Tyr Asn Val His Phe Ser Asn Lys Leu Pro Ala Arg Pro Gln Val
625                 630                 635                 640

Glu Lys Glu Phe Gly Phe Cys Cys Lys Lys Asp His
                645                 650
```

<210> SEQ ID NO 5
<211> LENGTH: 2849
<212> TYPE: DNA
<213> ORGANISM: Mus musculus

<400> SEQUENCE: 5

```
agagtaggaa gcaagctgca gggccacaga ccatcggaac taaaggtctg caggggaagt      60
tgcaggcagg gctggccact gcagctccca ggctccaacc tcccgcaatg cttcctgtgg     120
cttctggcac taggggtagc acccaggatc tgttccaggt tggcctagca cctccaggtc     180
ctgaagacta ccttgaggtc agcattccaa cagactcaag agccaagtat cctgaggaca     240
caagtggaca aagggaact gacgtcctag catctctgag accatctgtg cctcgggtac     300
tagtgcttcc tggggaaatt ccatgtgaga aacctggtga gatattcatt ctgttgaaag     360
atgaactaat tggcgaaatt ctagaggttg aatttatatc aaccaacaag cgcctcagag     420
cacggccagc acgttggaat aagagtgtct ggcatatgaa agctgcagat tttccagctg     480
gctcggtcac tgtcaatatc cactgtgatg gaatcatcaa ggccacaaca gagattaaat     540
actgttcagc agcaaaagca acagaaagtc catttagagt gtcagacccg ggcaagagtt     600
tgtgccagaa aagcatcgaa gaacttgata atgttcttgc atctatattc aagcgtgaga     660
taccatatta tgaattcaaa catctccaag ctgaaactta ccctcaaaaa gaacgtactc     720
acaccacaga gctcccaaca cttcttcact gtgcagcaaa atttggctta agaatctgg      780
ctcttcatct gctgcagtgt tcaggagcaa ccagggcagc tagaatgaag gcgacagatg     840
gttcagacct gctgcatatt gctgaaaggc atggtcatga gaactcaag gaagtctttg      900
aagactttct cagccaaaac actggcagaa atagcaagca agaaaatgac tatgaagaag     960
atgtaatctc atttttccaca tattcaccct ccatgccgtc tccggcatcc cttcatgaac    1020
tcaggaagac acacaggcgg aacacagaca gatctgagga gcctgaaagg tctgtggaga    1080
tgaaggagga agaagcaggt gctgaggcaa gacgcagcct gtcagagggt gaaagggaaa    1140
gctccgagaa ccagtatgac gatctgtatg ttttcatccc tggtttgac accgaaggca    1200
actctgaaga gcctctccca cactgcaggc cacctctgct gccaccacga ccaggcactg    1260
ctgcctccca gctagaaaga cctcacttta cctcacaagg aaaagtactg gaagaccaaa    1320
tggaaagaag tcaaaactgg aatgatctca atgcaagacc agagacaaga gaggaatcca    1380
```

```
gcagagaaga aaagaaagaa gaagcccagg aggaggagga agaagaagaa aacccatatg    1440
catttgcaga gactgaagac aatgagtatg acctgatact ggccagtaag agtgtcaaga    1500
aaagaactgg aaatcggtct ttcattataa acagaccacc ggctcccaca ccccggccca    1560
cgcacatccc tcccaaagaa gaaacaacac cttacatagc tcaagtgttc caacaaaagg    1620
cagcccgaag acaatctgat ggtgataagt tctacagtct acctaagaaa cccgacaaaa    1680
ctcggatgga gggcccaacc ttccctagta caagggatta tctgactact gggcaggaag    1740
aactgatcct cctgcaggag agagtcaaga atgggaaaat gtctgtggat gaagctctgg    1800
agaaatttaa acattggcag atgggaaaga gtggtctgga aatgattcag caggaaaagc    1860
tacggcaact acgagacaac attattggga aaaggccaga agatgaaaat gcctatgata    1920
aactgaccat tgtgcaccat ccaagtggta atactgccca caatgaaaat atgttgtaca    1980
acagtccatt caacagtaag tttcctgctc gaatccaagt tgaaaaggag tttggtttct    2040
gctgcaaaaa agatcattaa aaaagactat tataatcaaa ctcaagaatc tgccaacatg    2100
ttgcgcctcg gtgaagccag cctgcttctg gaatacctgg tctccagggc taatctgcat    2160
ggacacagga cacaagtgtg cctttggatt tcaaagtgtg ttagcaccac aatttattgg    2220
tactgtacca cttcagatgg atacaacaaa agatggagac tcatagcatt ctctgaaaat    2280
ccattcattt ttaccacaac ttttgccacc agagcacctc attctcccat cttgaaaatt    2340
aaagaaaaaa aatcagcaaa gttaaatgca gaatagcaaa attaaggacc caaactatat    2400
aggttattct tcctattctt cctccttcaa ctaagaacgt tttgcatatt tgctctttaa    2460
atgaccatct tctgtctgcc tttctcacat tcagagccat aatgttcttg tgatgccatg    2520
ttttcagata gcttctttta tttactgcct atttgcatgt acctttgaaa tgtactttta    2580
ttcgcagttt tcgttagttg atggtgtttt gtatttgggt gataagcaag cactctacca    2640
gtgcccaagt cttcagccct ctacacggat tcctgaagtc atgttaattc tatcaattaa    2700
tgacgtgcac agtaatattt cagaacatgg atgcctcgca cattgcctgt gctcatcctc    2760
tgctcttctg gaaggtattt ccccatgctt ccctgtcccc aaggacttac taaatgtctt    2820
tctctcaaat taaaaagtac ttttgcaaa                                      2849
```

<210> SEQ ID NO 6
<211> LENGTH: 650
<212> TYPE: PRT
<213> ORGANISM: Mus musculus

<400> SEQUENCE: 6

```
Met Leu Pro Val Ala Ser Gly Thr Arg Gly Ser Thr Gln Asp Leu Phe
1               5                   10                  15

Gln Val Gly Leu Ala Pro Pro Gly Pro Glu Asp Tyr Leu Glu Val Ser
            20                  25                  30

Ile Pro Thr Asp Ser Arg Ala Lys Tyr Pro Glu Asp Thr Ser Gly Gln
        35                  40                  45

Lys Gly Thr Asp Val Leu Ala Ser Leu Arg Pro Ser Val Pro Arg Val
    50                  55                  60

Leu Val Leu Pro Gly Glu Ile Pro Cys Glu Lys Pro Gly Glu Ile Phe
65                  70                  75                  80

Ile Leu Leu Lys Asp Glu Leu Ile Gly Glu Ile Leu Glu Val Glu Phe
                85                  90                  95

Ile Ser Thr Asn Lys Arg Leu Arg Ala Arg Pro Ala Trp Asn Lys
            100                 105                 110
```

-continued

```
Ser Val Trp His Met Lys Ala Ala Asp Phe Pro Ala Gly Ser Val Thr
    115                 120                 125
Val Asn Ile His Cys Asp Gly Ile Ile Lys Ala Thr Thr Glu Ile Lys
130                 135                 140
Tyr Cys Ser Ala Ala Lys Ala Thr Glu Ser Pro Phe Arg Val Ser Asp
145                 150                 155                 160
Pro Gly Lys Ser Leu Cys Gln Lys Ser Ile Glu Glu Leu Asp Asn Val
                165                 170                 175
Leu Ala Ser Ile Phe Lys Arg Glu Ile Pro Tyr Tyr Glu Phe Lys His
                180                 185                 190
Leu Gln Ala Glu Thr Tyr Pro Gln Lys Glu Arg Thr His Thr Thr Glu
                195                 200                 205
Leu Pro Thr Leu Leu His Cys Ala Ala Lys Phe Gly Leu Lys Asn Leu
    210                 215                 220
Ala Leu His Leu Leu Gln Cys Ser Gly Ala Thr Arg Ala Ala Arg Met
225                 230                 235                 240
Lys Ala Thr Asp Gly Ser Asp Leu Leu His Ile Ala Glu Arg His Gly
                245                 250                 255
His Glu Glu Leu Lys Glu Val Phe Glu Asp Phe Leu Ser Gln Asn Thr
                260                 265                 270
Gly Arg Asn Ser Lys Gln Glu Asn Asp Tyr Glu Glu Asp Val Ile Ser
            275                 280                 285
Phe Ser Thr Tyr Ser Pro Ser Met Pro Ser Pro Ala Ser Leu His Glu
    290                 295                 300
Leu Arg Lys Thr His Arg Arg Asn Thr Asp Arg Ser Glu Glu Pro Glu
305                 310                 315                 320
Arg Ser Val Glu Met Lys Glu Glu Ala Gly Ala Glu Ala Arg Arg
                325                 330                 335
Ser Leu Ser Glu Gly Glu Arg Glu Ser Ser Glu Asn Gln Tyr Asp Asp
            340                 345                 350
Leu Tyr Val Phe Ile Pro Gly Phe Asp Thr Glu Gly Asn Ser Glu Glu
        355                 360                 365
Pro Leu Pro His Cys Arg Pro Pro Leu Leu Pro Pro Arg Pro Gly Thr
    370                 375                 380
Ala Ala Ser Gln Leu Glu Arg Pro His Phe Thr Ser Gln Gly Lys Val
385                 390                 395                 400
Leu Glu Asp Gln Met Glu Arg Ser Gln Asn Trp Asn Asp Leu Asn Ala
                405                 410                 415
Arg Pro Glu Thr Arg Glu Glu Ser Arg Glu Glu Lys Lys Glu Glu
                420                 425                 430
Ala Gln Glu Glu Glu Glu Glu Glu Asn Pro Tyr Ala Phe Ala Glu
            435                 440                 445
Thr Glu Asp Asn Glu Tyr Asp Leu Ile Leu Ala Ser Lys Ser Val Lys
    450                 455                 460
Lys Arg Thr Gly Asn Arg Ser Phe Ile Ile Asn Arg Pro Pro Ala Pro
465                 470                 475                 480
Thr Pro Arg Pro Thr His Ile Pro Pro Lys Glu Thr Thr Pro Tyr
                485                 490                 495
Ile Ala Gln Val Phe Gln Gln Lys Ala Ala Arg Arg Gln Ser Asp Gly
            500                 505                 510
Asp Lys Phe Tyr Ser Leu Pro Lys Lys Pro Asp Lys Thr Arg Met Glu
        515                 520                 525
Gly Pro Thr Phe Pro Ser Thr Arg Asp Tyr Leu Thr Thr Gly Gln Glu
    530                 535                 540
```

-continued

```
Glu Leu Ile Leu Leu Gln Glu Arg Val Lys Asn Gly Lys Met Ser Val
545                 550                 555                 560

Asp Glu Ala Leu Glu Lys Phe Lys His Trp Gln Met Gly Lys Ser Gly
            565                 570                 575

Leu Glu Met Ile Gln Gln Glu Lys Leu Arg Gln Leu Arg Asp Asn Ile
        580                 585                 590

Ile Gly Lys Arg Pro Glu Asp Glu Asn Ala Tyr Asp Lys Leu Thr Ile
    595                 600                 605

Val His His Pro Ser Gly Asn Thr Ala His Asn Glu Asn Met Leu Tyr
610                 615                 620

Asn Ser Pro Phe Asn Ser Lys Phe Pro Ala Arg Ile Gln Val Glu Lys
625                 630                 635                 640

Glu Phe Gly Phe Cys Cys Lys Lys Asp His
                645                 650

<210> SEQ ID NO 7
<211> LENGTH: 28
<212> TYPE: DNA
<213> ORGANISM: Artificial Sequence
<220> FEATURE:
<223> OTHER INFORMATION: primer7

<400> SEQUENCE: 7
cacctcaacc gccacaatgc tgccagca                                     28

<210> SEQ ID NO 8
<211> LENGTH: 30
<212> TYPE: DNA
<213> ORGANISM: Artificial Sequence
<220> FEATURE:
<223> OTHER INFORMATION: primer8

<400> SEQUENCE: 8
ataataacct tctttaatga tctttcttgc                                   30

<210> SEQ ID NO 9
<211> LENGTH: 26
<212> TYPE: DNA
<213> ORGANISM: Artificial Sequence
<220> FEATURE:
<223> OTHER INFORMATION: primer9

<400> SEQUENCE: 9
agaggaaact acaccttaca tagctc                                       26

<210> SEQ ID NO 10
<211> LENGTH: 23
<212> TYPE: DNA
<213> ORGANISM: Artificial Sequence
<220> FEATURE:
<223> OTHER INFORMATION: primer10

<400> SEQUENCE: 10
gatgagttct tcctgaccat cag                                          23

<210> SEQ ID NO 11
<211> LENGTH: 24
<212> TYPE: DNA
<213> ORGANISM: Artificial Sequence
<220> FEATURE:
<223> OTHER INFORMATION: primer11

<400> SEQUENCE: 11
```

```
tcaaagcaga tgggagatct caac                                          24

<210> SEQ ID NO 12
<211> LENGTH: 21
<212> TYPE: DNA
<213> ORGANISM: Artificial Sequence
<220> FEATURE:
<223> OTHER INFORMATION: primer12

<400> SEQUENCE: 12
cagcgccccc agattctgaa g                                             21

<210> SEQ ID NO 13
<211> LENGTH: 20
<212> TYPE: DNA
<213> ORGANISM: Artificial Sequence
<220> FEATURE:
<223> OTHER INFORMATION: primer13

<400> SEQUENCE: 13
cagcgccccc aggaaataca                                               20

<210> SEQ ID NO 14
<211> LENGTH: 25
<212> TYPE: DNA
<213> ORGANISM: Artificial Sequence
<220> FEATURE:
<223> OTHER INFORMATION: primer14

<400> SEQUENCE: 14
gcctattctt tgttttggaa ataca                                         25

<210> SEQ ID NO 15
<211> LENGTH: 25
<212> TYPE: DNA
<213> ORGANISM: Artificial Sequence
<220> FEATURE:
<223> OTHER INFORMATION: primer15

<400> SEQUENCE: 15
cacatggaat tcagtggga agcac                                          25

<210> SEQ ID NO 16
<211> LENGTH: 24
<212> TYPE: DNA
<213> ORGANISM: Artificial Sequence
<220> FEATURE:
<223> OTHER INFORMATION: primer16

<400> SEQUENCE: 16
atcacagtag acattgacat ggac                                          24

<210> SEQ ID NO 17
<211> LENGTH: 24
<212> TYPE: DNA
<213> ORGANISM: Artificial Sequence
<220> FEATURE:
<223> OTHER INFORMATION: primer17

<400> SEQUENCE: 17
ttggagaggg tatttagagc cata                                          24

<210> SEQ ID NO 18
<211> LENGTH: 23
<212> TYPE: DNA
<213> ORGANISM: Artificial Sequence
<220> FEATURE:
```

<223> OTHER INFORMATION: primer18

<400> SEQUENCE: 18
aagcagggct accaattcac cag                                    23

<210> SEQ ID NO 19
<211> LENGTH: 25
<212> TYPE: DNA
<213> ORGANISM: Artificial Sequence
<220> FEATURE:
<223> OTHER INFORMATION: primer19

<400> SEQUENCE: 19
ctatgatact ggaaatactg tcagt                                  25

<210> SEQ ID NO 20
<211> LENGTH: 21
<212> TYPE: DNA
<213> ORGANISM: Artificial Sequence
<220> FEATURE:
<223> OTHER INFORMATION: primer20

<400> SEQUENCE: 20
agcatatgac cagctgatca g                                      21

<210> SEQ ID NO 21
<211> LENGTH: 25
<212> TYPE: DNA
<213> ORGANISM: Artificial Sequence
<220> FEATURE:
<223> OTHER INFORMATION: primer21

<400> SEQUENCE: 21
ttgatttact atgaaaatat caagc                                  25

<210> SEQ ID NO 22
<211> LENGTH: 23
<212> TYPE: DNA
<213> ORGANISM: Artificial Sequence
<220> FEATURE:
<223> OTHER INFORMATION: primer22

<400> SEQUENCE: 22
ttacataaga aaccagcttc cag                                    23

<210> SEQ ID NO 23
<211> LENGTH: 21
<212> TYPE: DNA
<213> ORGANISM: Artificial Sequence
<220> FEATURE:
<223> OTHER INFORMATION: primer23

<400> SEQUENCE: 23
acctcccgca atgcttcctg t                                      21

<210> SEQ ID NO 24
<211> LENGTH: 24
<212> TYPE: DNA
<213> ORGANISM: Artificial Sequence
<220> FEATURE:
<223> OTHER INFORMATION: primer24

<400> SEQUENCE: 24
acatggaatt tccccaggaa gcac                                   24

NUCLEIC ACID MOLECULES ENCODING BANK1 SPLICE VARIANTS

CROSS-REFERENCE TO RELATED APPLICATION

This application is the U.S. national stage application of International Patent Application No. PCT/EP2008/065980, filed Nov. 21, 2008, which claims the benefit of U.S. Provisional Patent Application No. 61/004,480, filed Nov. 28, 2007, the disclosures of which are hereby incorporated by reference in their entirety, including all figures, tables and amino acid or nucleic acid sequences.

The Sequence Listing for this application is labeled "SeqList.txt" which was created on Mar. 25, 2010 and is 29 KB. The entire contents of the sequence listing is incorporated herein by reference in its entirety.

FIELD OF THE INVENTION

The present invention relates to a new splice variant of BANK1, the use of SNPs associate with BANK1 for diagnostics and the use of antagonists to modulate BANK1 and/or the BANK1 pathway.

BACKGROUND OF THE INVENTION

Genetic techniques allow the identification of single nucleotide polymorphisms (SNPs) in individuals. SNPs are changes in a gene in one single nucleotide. Identification of SNPs can be correlated with a biological pathway having implications for a particular disease. The polymorphisms may be correlated also with a predisposition or risk for a disease by application of statistical analyses. Accordingly, targeting a particular biological pathway related to a disease is a means to treat such disease.

B-cell scaffold protein with ankyrin repeats (BANK1) is expressed in B cells and is tyrosine phosphorylated upon B-cell antigen receptor (BCR) stimulation. The BANK1 gene has 284 kb. BANK1 is an adaptor protein (6, 7) expressed mainly in B cells. The two full length isoforms of 785 and 755 amino acids, differ by 30 amino acids in the N-terminal region coded by the alternative exon 1A (FIG. 1e) and contain ankyrin repeat motifs and coiled-coil regions—structures highly similar between BANK1, BCAP and D of adaptor proteins (8). B cell activation through BCR engagement leads to tyrosine phosphorylation of BANK1, which in turn promotes its association with the protein tyrosine kinase Lyn and the calcium channel IP3R (3). BANK1 serves as a docking station bridging together and facilitating phosphorylation and activation of IP3R by Lyn and the consequent release of $Ca^{2+}$ from endoplasmic reticulum stores (3, 9). It was previously found that IP3R associates with the SNP rs10516487 lying within a region essential for binding of IP3R.

The BANK1 SNPs rs17266594 and rs3733197 have also been described in the literature.

None of the above SNPs have been described in the literature to be useful for the prediction of an inflammatory, auto-immune or neurological disease.

BANK1 and the pathway it is involved in, is considered to have implications for inflammatory and auto-immune disorders. In particularly, BANK1 is expressed in B-cells and therefore the pathway wherein BANK1 is involved has an implication for diseases associated with B-cells, e.g. Systemic Lupus Erythematosus (SLE). Multiple Sclerosis (MS) is related to T-cells, however, also the role of B-cells has been discussed in this disease. Accordingly, polymorphisms in the BANK1 gene may be used to diagnose a predisposition or risk for MS. Moreover, the BANK1 pathway may have implications for MS. In consequence, targeting this pathway and its modulation may represent a means to prevent or treat MS.

SUMMARY OF THE INVENTION

According to one aspect of the invention, a novel splice variant of BANK1 is provided.

According to another aspect of the invention, a method is provided for diagnosing an individual for the predisposition of, the risk of developing or suffering from an auto-immune or inflammatory disease wherein the pathway of BANK1 is involved.

According to another aspect of the invention, a method for the treatment and/or prevention of an auto-immune or inflammatory disease is provided using an antagonist targeting BANK1, the biological pathway of BANK1 and/or factors connected to the BANK1 pathway.

According to another aspect of the invention, a method of treating diseases is provided wherein the pathway of BANK1 is involved using an antagonist targeting BANK1, the biological pathway of BANK1 and/or factors connected to the BANK1 pathway.

BRIEF DESCRIPTION OF THE SEQUENCES AND DRAWINGS

SEQ ID NO: 1, 3, 5 are the nucleic acid sequences of the BANK1 delta 2 splice variant of human, chimpanzee and mouse, respectively.

SEQ ID NO: 2, 4, 6 are the amino acid sequences of the BANK1 delta 2 splice variant of human, chimpanzee and mouse, respectively.

FIG. 1a-1e. Association of rs17266594 with increased levels of the full-length isoform of BANK1. (a) Total expression of BANK1 gene in separated mononuclear cell subpopulations. (b) RT-PCR of the coding part of BANK1 amplified from total human spleen cDNA reveals two bands on a gel. 1 kb ladder (New England Biolabs) is shown on the left. The identity of both bands, 2.3 kb upper band and 1.9 kb smaller band, was confirmed by sequencing analysis. (c) Relative mRNA expression levels of the full-length and delta 2 isoforms of BANK1, as determined by quantitative real-time RT-PCR on total RNA purified from human PBMCs. Data represent mean±S.D. 39 individuals with TT for the branch point site SNP, 34 with TC and 10 with CC genotype were analysed. Full-length transcript: TT versus CC, P=0.0004 (Student's t-test); delta 2 transcript: TT versus CC, P=0.0088. (d) Total BANK1 expression was not significantly affected by SNP rs17266594. (e) Schematic structure of the 5'-end of the gene. SNP rs17266594 located in the branch point site of intron 1 alters splicing efficiency of the full-length and delta 2 transcripts. SNP rs10516487 results in non-synonymous substitution of $Arg_{61}$ to His. Alternative splicing gives rise to two isoforms, full-length and delta 2 with in-frame deletion of entire exon 2 of BANK1. Thus, the short protein isoform lacks the putative domain for IP3R binding and could function as a dominant negative isoform attenuating signaling from the full-length protein.

IP3R BD—inositol 1,4,5-triphosphate receptor binding domain, Lyn BD—tyrosine kinase Lyn binding domain.

Figure 2A:
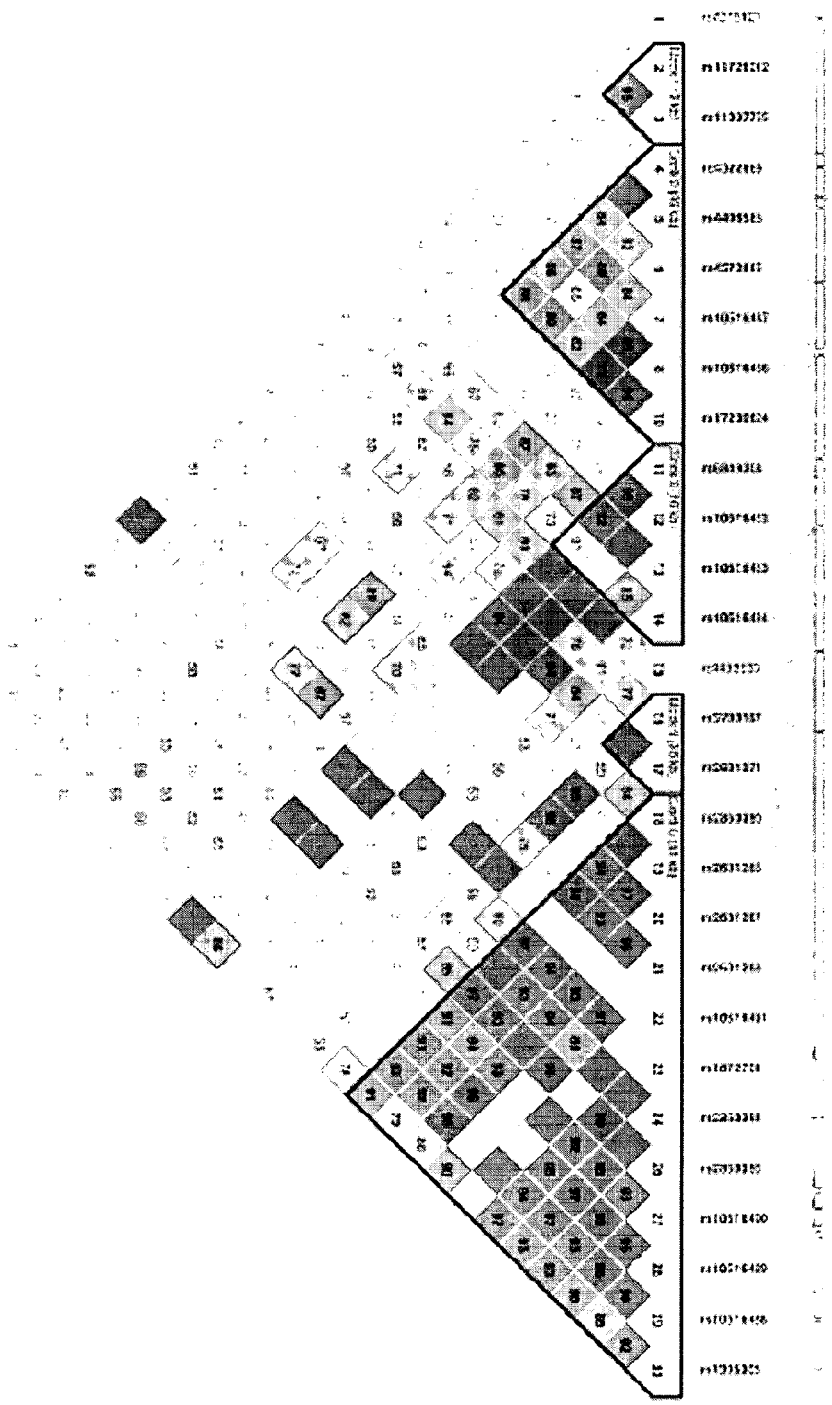

FIG. 2a Linkage disequilibrium and haplotype block structure across BANK1, Data calculated with Haploview analysis of our data using the Swedish cases and controls run for 30 SNPs across the gene.

Figure 2B:
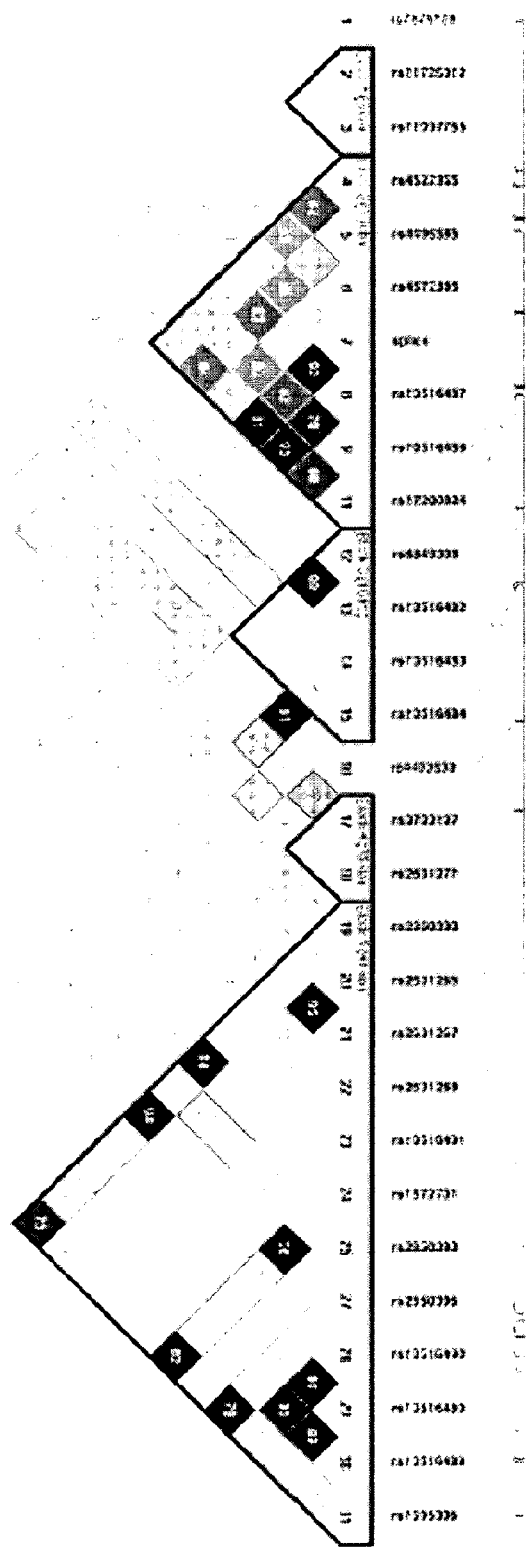

FIG. 2b R2 for all SNPs across BANK1.

Figure 2C:
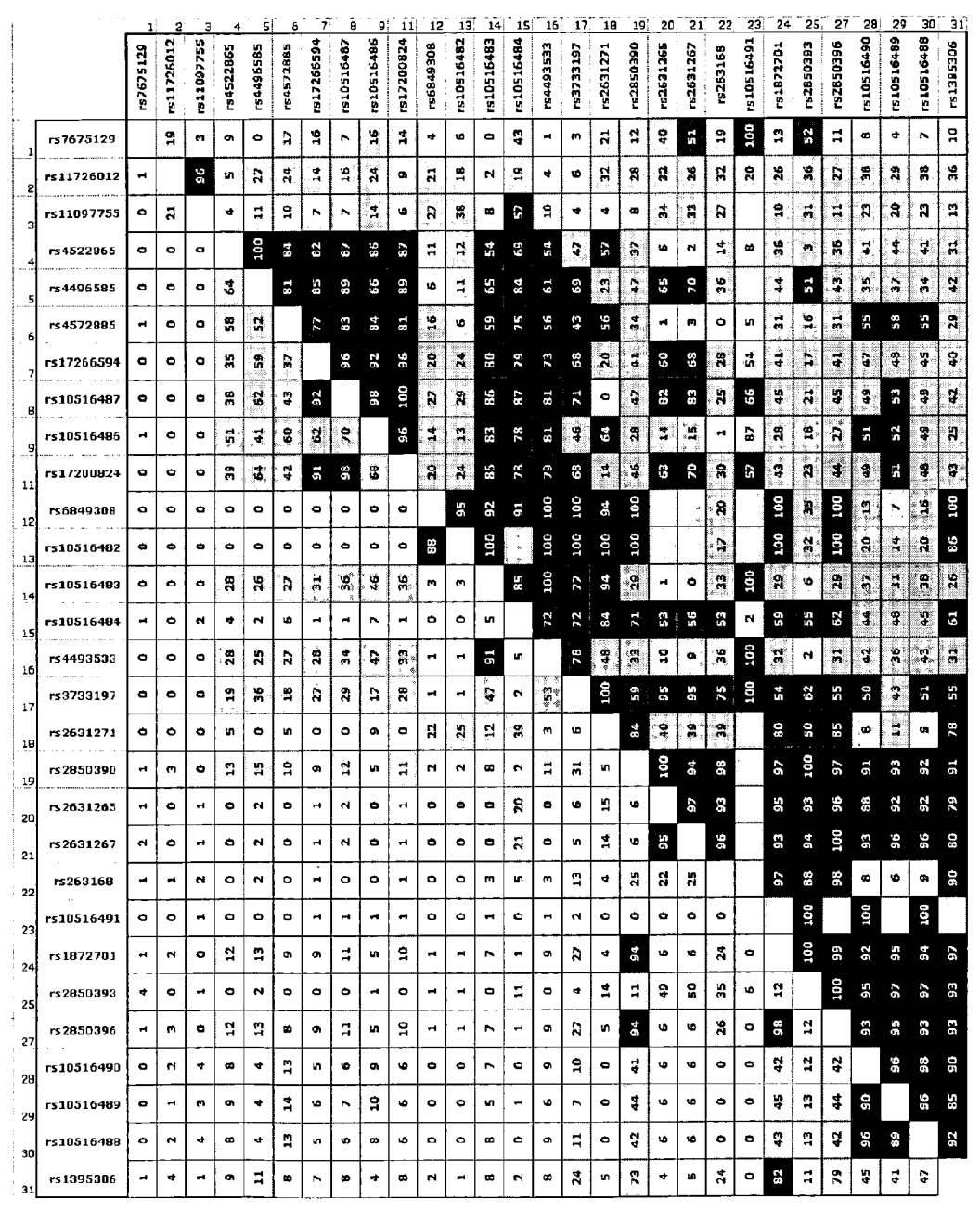

FIG. 2c FIGS. 2a and 2b (combined)

Figure 3:
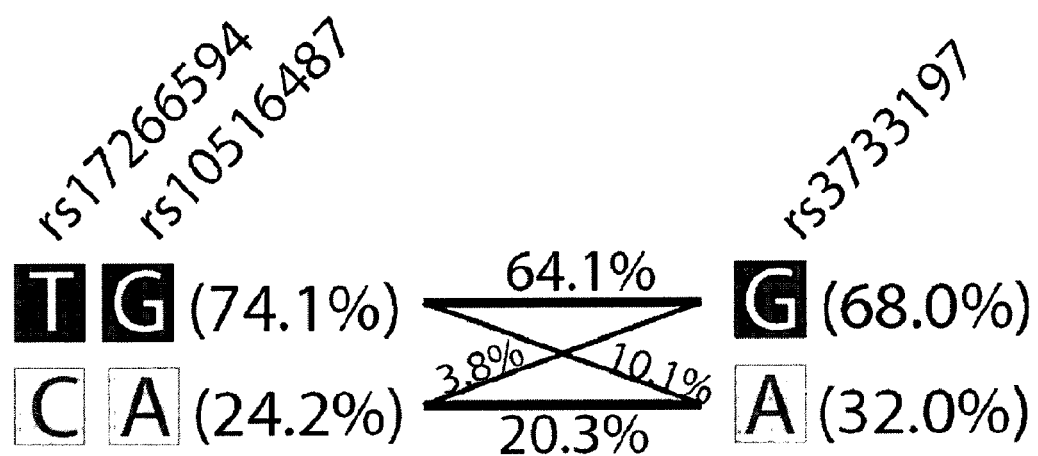

FIG. 3 Frequencies of the haplotypes constructed with rs17266594 and rs10516487 (74.1% TG, 24.2% CA), and allele frequencies for rs3733197 (68.0% G, 32.0% A). The figure also shows the frequencies of the haplotypes when including all three SNPs (64.1% TGG, 10.1% TGA, 20.3% CAA, 3.8% CAG). Data is calculated using all populations, combined.

DETAILED DESCRIPTION OF THE INVENTION

The following paragraphs contain definitions used according to the invention and are intended to apply uniformly throughout the specification and claims unless otherwise expressly set out definition provides a broader definition.

The present invention is directed to an isolated nucleic acid sequence comprising the sequence of BANK1 lacking exon 2. In a preferred embodiment the nucleic acid is of human, chimpanzee, or mouse origin. As a reference for the BANK1 sequence one may refer to Nature 431 (7011), 931-945 (2004).

In the human BANK1 sequence as described in NCBI's human genome assembly build 36, chromosome 4 the exons/introns are as follows:
Exon1: 102930919-102931130
Intron1: 102931131-102969987
Exon2: 102969988-102970386
Intron2: 102970387-102995214
Exon3: 102995215-102995369
Intron3: 102995370-103002705
Exon4: 103002706-103002844
Intron4: 103002845-103010684
Exon5: 103010685-103010824
Intron5: 103010825-103035484
Exon6: 103035485-103035590
Intron6: 103035591-103058172
Exon7: 103058173-103058369
Intron7: 103058370-103161693
Exon8: 103161694-103161772
Intron8: 103161773-103165380
Exon9: 103165381-103165689
Intron9: 103165690-103170139
Exon10: 103170140-103170445
Intron10: 103170446-103184018
Exon11: 103184019-103184087
Intron 11: 103184088-103200390
Exon12: 103200391-103200569
Intron12: 103200570-103203254
Exon13: 103203255-103203318
Intron13: 103203319-103211454
Exon14: 103211455-103211484
Intron14: 103211485-103212524
Exon15: 103212525-103212580
Intron15: 103212581-103213863
Exon16: 103213864-103213928
Intron16: 103213929-103214184
Exon17: 103214185-103214918

It is preferably possible that only part of the BANK1 exon 2 is deleted. Such a molecule is equally useful according to the invention.

In one embodiment the isolated nucleic acid comprises SEQ ID NO: 1, 3, or 5, or the complement of said nucleic acid sequence.

In one embodiment the invention relates to an isolated nucleic acid which:

a) hybridizes under high stringency conditions; or
b) exhibits at least about 85%, preferably at least about 90% and more preferably at least 95% identity over a stretch of at least about 30 nucleotides with a nucleic acid selected from the group consisting of SEQ ID NO: 1, 3, or 5, or a complement of said nucleic acid sequence.

Another embodiment of the invention is a polypeptide encoded by any of the nucleic acid sequences as mentioned above.

Another embodiment is a vector comprising a nucleic acid as described above, preferably a nucleic acid selected from the group consisting of SEQ ID NO: 1, 3, or 5, or a complement of said nucleic acid sequence.

Preferably the vector containing said nucleic acid molecule is operatively linked to at least one expression control sequence allowing expression in prokaryotic or eukaryotic host cells of the encoded polypeptide.

Another embodiment is a host cell transformed with a vector or a nucleic acid as described above.

Yet another embodiment of the invention is a method for making a polypeptide as described above comprising culturing a host cell as defined above under conditions in which the nucleic acid is expressed, and recovering the polypeptide encoded by said nucleic acid from the culture.

Another embodiment is a method for genotyping comprising the steps of:

a. Isolating a nucleic acid from a sample of an individual; and
b. Determining whether in rs10516487 a guanine or an adenine is present, in rs17266594 a tyrosin or a cytosine is present, in rs3733197 an adenine or a guanine is present in the biallelic marker.

In a preferred method the identity of the nucleotides at said biallelic markers is determined for both copies of said biallelic markers present in said individual's genome.

The method for genotyping according to the invention is preferably performed by a microsequencing assay. The method preferably further comprises amplifying a portion of a sequence comprising the biallelic marker prior to said determining step. Preferably said amplifying is performed by PCR. The method according to the invention further comprises the step of correlating the result of the genotyping steps with a risk of suffering or a predisposition for an auto-immune disease or inflammatory disease.

In a preferred embodiment the method is performed, wherein the presence of a guanine in rs10516487, a tyrosine in rs17266594 and an adenine in rs3733197 in said individual indicates that said individual suffers from, has a predisposition for or is at risk of suffering from said auto-immune disease or inflammatory disease.

The method of the invention preferably is applied wherein the disease is Systemic Lupus Erythrematosus or Multiple Sclerosis.

Now that the inventors have established the association between BANK1 and SLE and MS or related diseases, it should be understood that additional susceptibility alterations can be identified within said gene or polypeptide, e.g., following the methodology disclosed in the examples.

The presence of an alteration in the BANK1 gene may be detected by any technique known per se to the skilled artisan, including sequencing, pyrosequencing, selective hybridisation, selective amplification and/or mass spectrometry including matrix-assisted laser desorption/ionization time-of-flight mass spectrometry (MALDI-TOF MS) (Gut et al., 2004). In a particular embodiment, the alteration is detected by selective nucleic acid amplification using one or several specific primers. The alteration is detected by selective hybridization using one or several specific probes.

Further techniques include gel electrophoresis-based genotyping methods such as PCR coupled with restriction fragment length polymorphism analysis, multiplex PCR, oligonucleotide ligation assay, and minisequencing; fluorescent dye-based genotyping technologies such as oligonucleotide ligation assay, pyrosequencing, single-base extension with fluorescence detection, homogeneous solution hybridization such as TaqMan, and molecular beacon genotyping; rolling circle amplification and Invader assays as well as DNA chip-based microarray and mass spectrometry genotyping technologies (Shi et al., 2001).

Furthermore, RNA expression of altered genes can be quantified by methods known in the art such as subtractive hybridisation, quantitative PCR, TaqMan, differential display reverse transcription PCR, serial, partial sequencing of cDNAs (sequencing of expressed sequenced tags (ESTs) and serial analysis of gene expression (SAGE)), or parallel hybridization of labeled cDNAs to specific probes immobilized on a grid (macro- and microarrays and DNA chips. Particular methods include allele-specific oligonucleotide (ASO), allele-specific amplification, fluorescent in situ hybridization (FISH) Southern and Northern blot, and clamped denaturing gel electrophoresis.

Protein expression analysis methods are known in the art and include 2-dimensional gel-electrophoresis, mass spectrometry and antibody microarrays (Freeman et al., 2004 and Zhu et al., 2003).

Sequencing can be carried out using techniques well known in the art, using automatic sequencers. The sequencing may be performed on the complete gene or, more preferably, on specific domains thereof, typically those known or suspected to carry deleterious mutations or other alterations.

Amplification may be performed according to various techniques known in the art, such as by polymerase chain reaction (PCR), ligase chain reaction (LCR) and strand displacement amplification (SDA). These techniques can be performed using commercially available reagents and protocols. A preferred technique is allele-specific PCR.

Nucleic acid primers useful for amplifying sequences from the BANK1 gene are able to specifically hybridize with a portion of the BANK1 gene that either flanks or overlaps with a susceptibility alteration. The primer sequence overlaps with the alteration when said alteration is contained within the sequence of the BANK1 gene to which the primer hybridizes. The primer sequence flanks the alteration when the primer hybridizes with a portion of the BANK1 gene that is preferably located at a distance below 300 bp of said alteration, even more preferably below 250, 200, 150, 100, 50, 40, 30 or 20 bp from said alteration. Preferably, the primer hybridizes with a portion of the BANK1 gene that is at 5, 4, 3, 2, 1 bp distance or immediately adjacent to said alteration.

In another embodiment the method for detecting whether an individual has a predisposition for or is at risk of an auto-immune disease or inflammatory disease according to the invention comprises the steps:
  a. Isolating the nucleic acid of an individual;
  b. Detecting and quantifying the BANK1 full length nucleic acid;
  c. Detecting and quantifying the BANK1 delta 2 nucleic acid;
  d. Determining the ratio b./c. and/or c./b. of the results of step b. and c.

In this method the nucleic acid is preferably a mRNA, cRNA or cDNA.

In step d. of the above method the determined ratio is an indication of the disease or its increased susceptibility. The more full length mRNA and the less delta 2 splice variant the more risk of disease an individual has. In particular, the higher this ratio is in the b./c. correlation and the lower this ratio is in the c./b. correlation the higher is the risk to develop an auto-immune or inflammatory diseases, in particular SLE or MS.

The inventors have found that the total BANK1 mRNA is not influenced by the presence of particular SNPs. IN particular SNPs rs10516487, rs17266594 and rs3733197 do not change the total amount of BANK1 mRNA content. Accordingly the ratio of full length to delta 2 splice variant of BANK1 mRNA or cDNA is not influenced by the presence of the SNPs of the invention. Preferably the ratio b./c. or c./b is about 1. The ratios useful in the invention are as described above either b./c. or c./b.

A change in rs17266594 from TT to TC to CC has an influence in the amount of delta 2 BANK1 splice variant mRNA detectable. A ration of b./c. greater than 1, preferably significantly greater than 1 is indicative of a suffering from, or a predisposition for auto-immune or inflammatory diseases, preferably Systemic Lupus Erythrematosus or Multiple Sclerosis. A ration of c./b. less than 1, preferably significantly less than 1 is indicative of a suffering from, or a predisposition for auto-immune or inflammatory diseases, preferably Systemic Lupus Erythrematosus or Multiple Sclerosis. A change in this SNP from TT to CC may be most reliably be used to make this prediction. The suffering or predisposition may be expressed by calculation of the odd ration (OD). It will be appreciated by the skilled person that any method detecting and/or calculating a change in the SNP rs17266594 and/or mRNA or cDNA of BANK1 full length and/or delta 2 splice variant may be used to detect a predisposition for auto-immune or inflammatory diseases. In one embodiment the invention may be applied by comparing the mRNA of the BANK1 delta 2 splice variant of a sample with a control. The control may be chosen from one sample or a number of pooled samples.

The SNPs rs10516487 and rs3733197 can also be used to predict a suffering or predisposition and may serve as indirect markers. According to the invention also other SNPs may be used as predictive markers if a linkage with the above markers can be detected. Such a linkage, preferably strong linkage, is expressed by the LD and is preferably D' 0.7, preferably D' 0.8, more preferably D' 0.9. Such markers can be identified by standard techniques known in the art.

In another embodiment the invention relates to a method for the treatment and/or prevention of diseases selected from auto-immune or inflammatory diseases using an antagonist targeting BANK1, the biological pathway of BANK1 and/or factors connected to the BANK1 pathway. Preferably disease is Systemic Lupus Erythrematosus or Multiple Sclerosis.

The antagonist may be any molecule that antagonizes partly or essentially completely the targets of interest. Preferably the antagonist targets BANK1, LYN and/or IP3R or their interaction. Preferably the antagonist targets the nucleic acid of BANK1. In one embodiment the antagonist is an anti-sense RNA, siRNA, an Aptamer, a peptide or a small molecule. In another embodiment the antagonist is an antibody or antibody fragment specifically binding to the targets BANK1, LYN and/or IP3R. Particularly preferred is an antagonist that binds specifically to IP3R or interferes with the function of IP3R. In this manner it can be preferably achieved that the impact of B-cells involved in the disease development or manifestation of the disease is positively modulated, preferably inhibited.

The preferred SNPs as used in the invention are as follows:

| Biallelic marker | Alternative nucleotides |
|---|---|
| rs10516487 | G/A |
| rs17266594 | T/C |
| rs3733197 | A/G |

The risk allel of rs10516487 is G. The risk allel of rs17266594 is the T and of rs3733197 is A. It will be understood that also other SNPs in Linkeage Disequilibrium (LD) may be used in the sense of the invention as described herein.

All references cited in this application are herewith incorporated by reference. In the following the present invention shall be illustrated by means of the following examples, which are not construed to be viewed as limiting the scope of the invention.

EXAMPLES

A set of 279 Swedish cases with SLE and 515 Swedish controls were genotyped for the 100 k Affymetrix SNPs array. After filtering, data from 85042 SNPs was used. As our purpose was to identify non-MHC genes and important functional polymorphisms, we proceeded to perform an analysis of the genomic location of the associated SNPs within known genes, discarding genomic deserts. Analysis of the data showed that among all the non-MHC-associated SNPs, one (rs10516487) was a non-synonymous substitution of arginine to histidine (triplet cGc→cAc, Arg→His) at amino-acid position 61 (from exon1A) of the BANK1 translated protein (allelic association, $P=6.4 \times 10^{-3}$; genotypic association, $P=2.01 \times 10^{-2}$). This SNP was ranked as #679 across the whole genome scan in the allelic association analysis and as #2148 in the genotypic test. The estimated FDR (False Discovery Rate) was 71.1% and 77.5% for these selections, respectively (2). Four more SNPs within BANK1 showed also association with SLE in the Affymetrix scan (Supplementary Table 1). The described B cell-specific expression of BANK1 and its potential role in B cell receptor-mediated activation led us to pursue this gene (3, 4).

We genotyped 30 SNPs in Swedish cases and 352 controls including the Affymetrix SNPs covering the complete 284 kb of the BANK1 gene. Two SNPs were not polymorphic in our population. Individual SNP analysis showed that 9 SNPs including rs10516487 were associated (Table 1). Using the solid-spine LD (Linkage Disequilibrium) haplotype block definition available from Haploview, 5 LD blocks could be recognized. All of the SNPs showing genetic association were lying on block 2, 3 and 4. No genetic association was detected for SNPs located in block 5 (Table 1, Supplementary Table 2 and FIG. 2a). To confirm the genetic association, we genotyped four more sets of cases and controls from Germany, Spain, Italy and Argentina for rs10516487. We could corroborate the genetic association with all the European sets, although the Argentine set showed a clear tendency without reaching significance (Table 2). We performed homogeneity and combinability analysis of the sets using the Breslow-Day method. As the data could be combined, a meta-analysis was performed on all the sets comprising 3971 individuals. The Mantel-Haenzel (MH) test revealed a P value reaching genome-wide significance and a pooled odds ratio of 1.38 ($X^2=39.243$, $P=3.74 \times 10^{-10}$, 95% CI 1.25-1.53) for the allelic association. A significant genotypic association was also observed (Table 2).

Figure 1B:
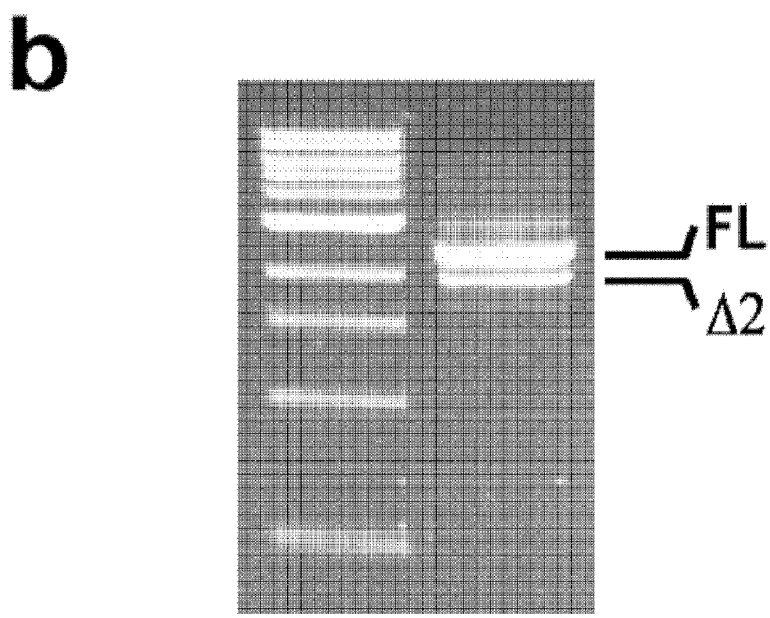

We initiated a detailed analysis of BANK1 expression and structure. We observed that indeed and as described, BANK1 is primarily expressed in CD19+ B cells at high levels, while very low expression could be detected in CD4+, CD8+ and CD14+ cells (FIG. 1a). We then sequenced the proximal promoter region, exon1A, exon1B, and exon2 (where haploblock 2 is located) and 500 bp up and downstream of these exons in 24 SLE patients and 8 controls. No novel SNPs were found for these regions. In order to clone BANK1 cDNA in an expression vector for functional analysis, we amplified full-length cDNA with distal primers. Surprisingly, two bands were detected on a gel after PCR (FIG. 1b). Subsequent cloning and sequencing revealed a new isoform with an in-frame deletion of the entire exon 2 (delta 2 isoform of BANK1). We analyzed cDNA from 83 healthy individuals and 30 SLE patients and found that this isoform was present in each sample, indicating that it is constitutively spliced. Moreover, this isoform was detected by PCR amplification of cDNA from chimp and mouse spleen as well, suggesting its conserved expression across species. Thus, we detected transcripts for three BANK1 isoforms, two full-length using exon1A or exon1B and a delta 2 isoform.

Figure 1C:
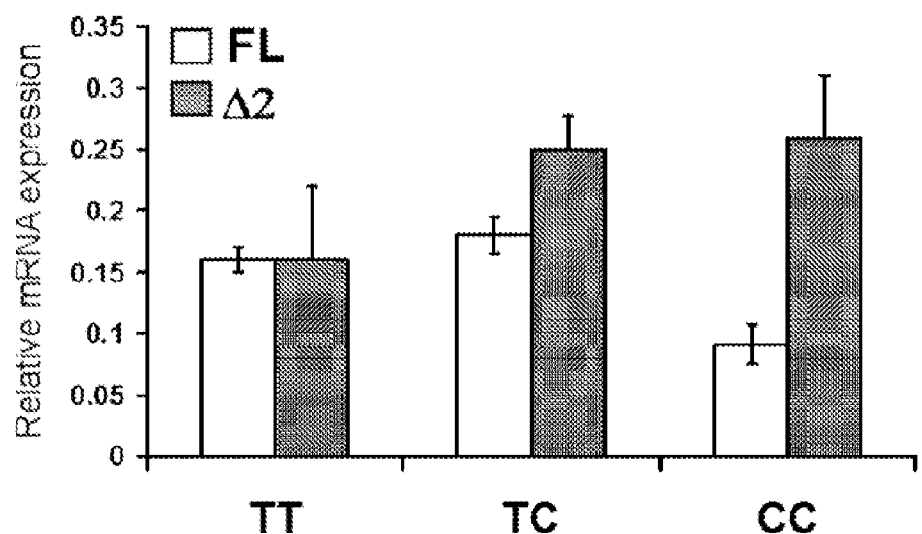
Figure 1D:
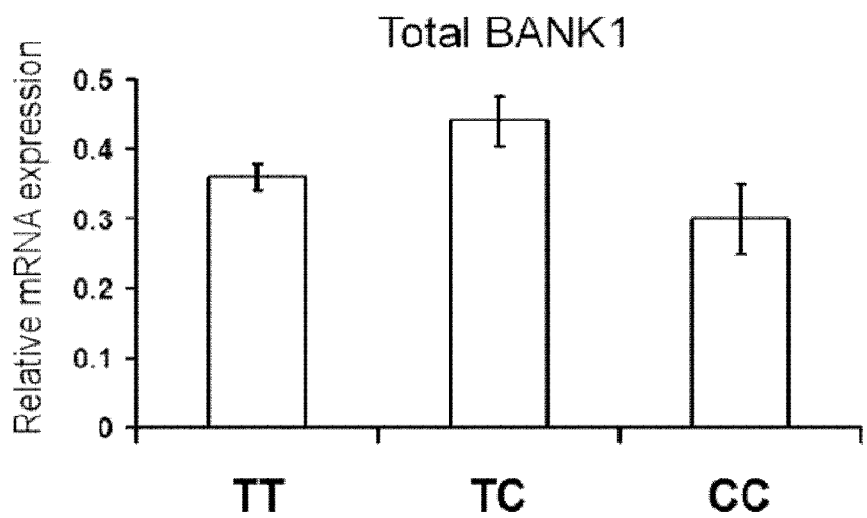

We next performed quantitative analysis of isoform expression in peripheral blood mononuclear cells. First, the relative levels of the two full-length isoforms, beginning with exon 1A and exon 1B, were determined. Since the latter transcript was present at very low levels, we continued the analysis measuring common full-length isoform levels. We noticed that the ratio of the full-length (FL) isoform to delta2 was not constant, which would be expected if delta 2 were equally expressed regardless of the genotypes of the analyzed samples. On the contrary, samples could be divided into groups according to the FL/delta 2 isoform ratio. After close examination of the genomic sequences surrounding exon 2 where putative signals affecting splicing could be located, one SNP, rs17266594, was found to lie in the putative branch point site and could potentially affect splicing. When expression data was re-grouped according to this SNP, a clear difference between the genotypes could be observed (FIG. 1c). Individuals homozygous for the T allele and thus having the classical structure of the branch point site (5) (YNYTG AYYN), showed equal expression of both isoforms, while expression of the full-length transcript was significantly suppressed (up to 40%) with concomitant upregulation of delta 2 isoform expression in individuals homozygous for the minor allele C. Total BANK1 transcription level was not significantly affected by the SNP (FIG. 1d). Genotyping of all of our sets of cases and controls for rs17266594 showed that the T allele was associated with SLE (Table 2; $P=4.74 \times 10^{-11}$, OR=1.42; 95% CI 1.28-1.58).

Both SNPs, rs17266594 and rs10516487, are separated by 153 nucleotides (nt) and are in strong LD (D'=0.95; R2=0.90; FIG. 2b). The T allele of the first SNP and the G allele of second one were found in the same risk haplotype associated with SLE (Table 2, bottom; $P=4.75 \times 10^{-6}$; OR=1.30, 95% CI 1.16-1.45) and FIG. 3.

We identified five non-synonymous substitutions in the databases. While most SNPs were non-polymorphic, one, rs3733197, an alanine to threonine substitution in amino acid position 383 (triplet Gca→Aca) in exon 7 coding for the ankyrin repeat-like motif, showed association in the combined sample ($X^2=16.576$; $P=4.67 \times 10^{-5}$ (OR=1.23, 95% CI 1.11-1.36;) although it had not shown association in our first analysis on Swedish individuals nor in the whole Scandinavian set (Table 1 and Supplementary Table 3). This SNP is in haploblock 4 (FIG. 2a) 88211bp apart from rs10516487 (D'=0.72; R2=0.39) and rs17266594 (R2=0.27), could segregate with the risk haplotype composed of the other two SNPs in some cases (FIG. 3) and could be a minor functional polymorphism.

Figure 1E:
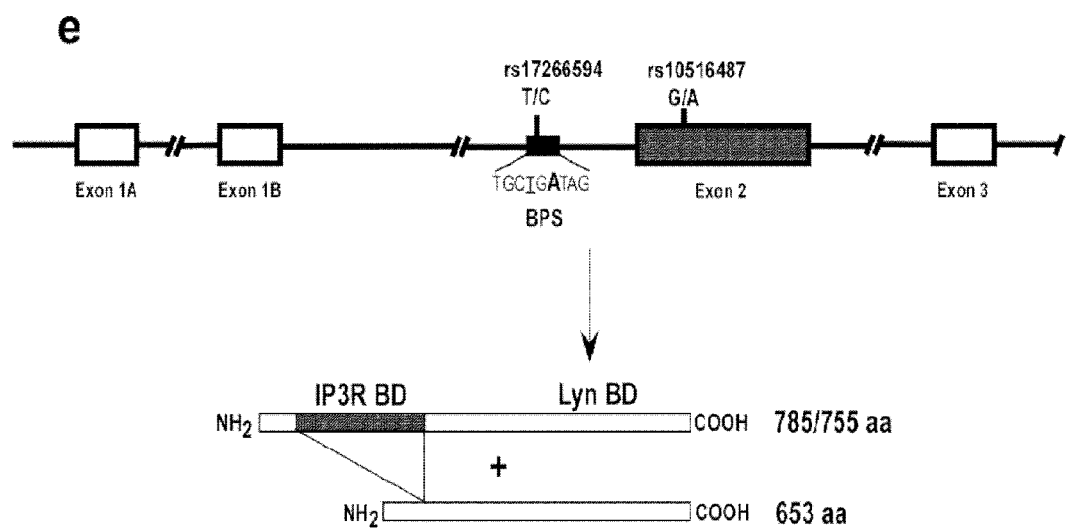

Thus, herein we identify three functional polymorphisms in BANK1 associated with SLE. The associated T allele of rs17266594 correlates with increased levels of the full-length isoform of BANK1. Thus, both polymorphisms in combination would lead to the achievement of one effect—high expression of a "more active" protein—through more efficient splicing of the full-length transcript that encodes a protein with an arginine residue in the IP3R binding domain. Since the delta 2 isoform lacks the entire exon 2 coding for IP3R binding and PH domains, it possibly functions as a dominant negative isoform thereby attenuating BANK1-mediated signaling (FIG. 1e).

Importance of mutations in ankyrin motifs for interaction with IP3R was recently highlighted by the discovery linking single amino acid substitutions in the adaptor protein ankyrin-B with cardiac arrhythmia and sudden cardiac death (10). While the alanine is associated with SLE, the rare allele A of rs3733197 might create a potential site for threonine kinases (11).

B cells are the major cell type affected in SLE. Novel therapies are aimed at depleting hyperactivated B cells that may function not solely as autoantibody producing cells, but also as important regulators of the innate and adaptive immune responses through antigen presentation and cytokine-mediated signaling (12). Functional and expression abnormalities of signaling molecules in B cells have been described in lupus. Of particular interest is the fact that Lyn, a binding partner of BANK1 is of key importance in human and mouse lupus autoimmune disease (13-18)

B cell hyperresponsiveness or a lack of control of B cell activation during immune responses. The precise role of BANK1 in BCR-mediated signaling remains unclear since two reports published so far contain conflicting data regarding the stimulatory or inhibitory role of BANK1 on B cell activation. Given the previously unreported existence of the alternative splicing of exon 2 we can speculate that the negative role for BANK1 assigned for the KO model was in part because of the remaining expression of the delta 2 isoform, as this exon was targeted by the KO-construct (4).

DNA Samples 279 cases and 515 controls were genotyped for the 100 k array. Of these individuals 279 cases and 352 controls were typed for the BANK1 coverage shown in Table 1.

For the functional polymorphisms an additional 185 Swedish patients were genotyped and 465 of the controls were available for genotyping of rs17266594 and rs3733197. We also added for the final MH (Mantel Haentsel) analysis and OR (Odds Ratio) estimation 84 Danish cases with the Swedish cases comprising the Scandinavian set shown in Table 2. The replication sets included 384 North German patients and 374 controls, 288 Argentine patients and 372 controls, 286 Italian patients and 252 controls. The Spanish cohort included 799 patients and 542 controls from several regions in Spain. 707 of the patients and 469 of the controls were genotyped for rs10516487 and rs3733197, and 678 of the patients and 457 of the controls for rs17266594. The reason for this is that DNA from a number of controls was not available. The German, Spanish and Argentine patients have all been previously described (19). The Italian cases are a multicenter collection of patients and their matched controls from Rome, Siena, Milan and Naples, that is North and Mid-Italy. All patients fulfil the 1982 ACR (American College of Rheumatology) criteria for the classification of SLE (20).

Genotyping

Genotyping of the 100 k Affymetrix array was performed according to the manufacturers instructions. Fine mapping and replication for SNPs rs10516487, rs17266594 and rs3733197 were done using TaqMan SNP genotyping assays (Applied Biosystems, Foster City, Calif.). The Affymetrix genotyping and fine mapping were performed at Serono Genetics Institute in Evry, France (now MerckSerono SA). The functional polymorphism replications were done. One hundred and six of samples were genotyped twice for verification showing 100% concordance. Genotyping success rate for all the samples was over 92%.

Statistical Analysis

For the 100K Affymetrix whole-genome scan analysis, pre-processing filters have been applied: SNPs have been discarded if (i) the proportion of missing genotypes is higher than 5%, (ii) the relative minor allele frequency is lower than 1% or (iii) the probability that the observed genotype distribution results from sampling a SNP which follows the Hardy-Weinberg equilibrium is lower than 0.02. Only SNPs from autosomal chromosomes have been kept for the sake of homogeneity between male and female individuals. SNP sequences have been mapped onto NCBI 36 human genome assembly and SNPs with multiple localizations have been discarded. For each remaining SNP, genotypic and allelic frequencies in cases and controls are calculated and the corresponding probability values are computed using exact (non-asymptotic) and unbiased algorithms (21). The False-Discovery Rate (FDR) is then estimated using the method described by Former, et al. (2).

For fine mapping analyses, genetic association, haplotype estimation, LD and R2 were all estimated using Haploview (v4.0RC2). The Breslow-Day test of combinability and the Mantel-Haenzel test were performed using the StatsDirect software (v2.4.6). As the Breslow-Day test showed combinability of the strata, the MH test for fixed effects was used in the analysis. Haplotypes were estimated using the PHASE software (v2.1) (22, 23). Genotypic odds ratios were calculated using the Unphased software (v3.0.9) (24).

Sequencing

DNA fragments for sequencing were amplified with the corresponding primers (see Supplementary Table 4), purified from agarose gel with QIAquick gel extraction kit (Qiagen) and sequenced using BigDye Terminator 3.1 (Applied Biosystems) at the Uppsala Genome Center.

RNA Purification and BANK1 Expression Analysis

Total RNA was purified with TRIZOL Reagent (Invitrogen) from peripheral blood mononuclear cells (PBMCs) obtained with agreed consent from healthy donors and lupus patients. 2 µg of RNA were reverse-transcribed with 2 U of MultiScribe transcriptase in PCR buffer II containing 5 mM $MgCl_2$, 1 mM dNTPs, 0.4 U of RNase inhibitor and 5 µM oligo-dT. All reagents were purchased from Applied Biosystems. cDNA synthesis was performed at 42° C. for 80 min, and then the reaction was terminated at 95° C. for 5 min. All cDNA samples were diluted to 15 ng/µl.

BANK1 expression was determined by real-time PCR on an ABI PRISM 7700 Sequence Detector (Applied Biosystems) with SDS 1.9.1 software. Total Bank1, both alternative full-length isoforms and delta2 isoform were quantified with SYBR Green and relevant primers (see Supplementary Table 4). We performed initial denaturation at 95° C. for 5 min followed by 45 cycles of PCR (95° C. for 15 s, 62° C. for 15 s and 72° C. for 30 s). PCR buffer provided with enzyme was supplemented with 3 mM $MgCl_2$, 200 μM of each of dNTPs, primers, SYBR Green (Molecular Probes), 15 ng of cDNA and 0.5 U of Platinum Taq polymerase (Invitrogen). Expression levels were normalized to the levels of TBP in the same samples amplified with commercial reagents (Applied Biosystems). All experiments were run in triplicate. Independent cDNA synthesis was carried out twice.

Cloning of Human, Mouse and Chimpanzee BANK1 delta 2 Isoform

Purification of total RNA from mouse spleen and cDNA synthesis were conducted as described above for the human PBMCs. Total RNA from chimpanzee (*Pan troglodytes*) spleen was kindly provided by Drs. Tomas Bergström and Lucia Cavelier, Uppsala University. Human gene was amplified from Human Spleen BD Marathon-Ready cDNA (Clontech). After initial denaturation at 95° C. for 5 min, 35 cycles (95° C. for 20 s, 60° C. for 15 s and 72° C. for 2 min 30 s) were performed in PCR buffer containing 2 mM $MgSO_4$, 200 μM of each of dNTPs, 0.4 μM of each of the corresponding primers (see Supplementary Table 4), and 0.5 U of Platinum Taq-High Fidelity enzyme (Invitrogen). Chimp cDNA was amplified with human-specific primers. PCR products were purified from agarose gel and cloned in pCR 4-TOPO vector (Invitrogen) according to the manufacturer's instructions. Plasmid DNA from positive clones was purified with QIAprep Spin Miniprep kit (Qiagen) and verified by sequencing.

Accession Codes

BANK1 delta 2 transcripts were deposited in Genbank under the following accession numbers EU051376 for human, EU051377 for chimpanzee and EU051378 for mouse.

URLs. Haploview: www.broad.mit.edu/mpg/haploview/; GraphPad Software: http://www.graphpad.com; Protein analysis: http://www.ebi.ac.uk/saps/; http://smart.embl-heidelberg.de/, http://ca.expasy.org/prosite/, http://www.cbs.dtu.dk/services/NetPhos/.

TABLE 1

Association of SNPs in BANK1 in Swedish SLE

| SNP rs name | Associated allele | Chi Sq | P Value |
|---|---|---|---|
| rs7675129 | T | 0.147 | 0.701 |
| rs11726012 | G | 0.495 | 0.4963 |
| rs11097755 | C | 0.406 | 0.524 |
| rs4522865 | A | 4.758 | 0.0292 |
| rs4496585 | A | 1.933 | 0.1644 |
| rs4572885 | T | 4.442 | 0.0355 |
| rs10516487 | G | 7.185 | 0.0074 |
| rs10516486 | C | 10.041 | 0.0015 |
| rs17200824 | A | 2.780 | 0.0955 |
| rs6849308 | C | 7.347 | 0.0067 |
| rs10516482 | C | 8.709 | 0.0032 |
| rs10516483 | C | 9.121 | 0.0025 |
| rs10516484 | A | 0.577 | 0.4476 |
| rs4493533 | C | 0.833 | 0.3614 |
| rs3733197 | A | 0.006 | 0.9402 |
| rs2631271 | G | 6.793 | 0.0092 |
| rs2850390 | C | 1.032 | 0.3096 |
| rs2631265 | T | 0.001 | 0.9815 |
| rs2631267 | G | 0.048 | 0.827 |
| rs2631268 | T | 1.375 | 0.2409 |
| rs10516491 | C | 2.388 | 0.1223 |
| rs1872701 | G | 1.454 | 0.2278 |
| rs2850393 | T | 0.313 | 0.5759 |
| rs2850396 | C | 0.344 | 0.5575 |
| rs10516490 | G | 0.311 | 0.5769 |
| rs10516489 | T | 0.312 | 0.5712 |
| rs10516488 | G | 0.537 | 0.4635 |
| rs1395306 | T | 1.739 | 0.1872 |

SUPPLEMENTARY TABLE 1

BANK1 SNPs in the 100k Array

| SNP | rs number | Position | (-log) P value |
|---|---|---|---|
| SNP_A-1701374 | rs10516487 | 103108254 | 2.27 |
| SNP_A-1701494 | rs10516486 | 103108454 | 2.79 |
| SNP_A-1664926 | rs6849308 | 103133261 | 2.22 |
| SNP_A-1706628 | rs10516482 | 103137348 | 2.52 |
| SNP_A-1744756 | rs10516483 | 103149083 | 3.25 |
| SNP_A-1683131 | rs2631271 | 103271574 | n.s. |
| SNP_A-1697391 | rs10516489 | 103331537 | n.s. |

TABLE 2

Genotypic, Allelic and Haplotypic Association of rs10516487 (R61H) and rs17266594 in five sets of SLE cases and controls and joint analysis with Mantel-Haenz

| | Population | | GG | GA | AA | Chi square | P-Value | Odds ratio (CI) a | Allele G | Allele A | P-Value | Odds ratio (CI) |
|---|---|---|---|---|---|---|---|---|---|---|---|---|
| rs10516487 | Scandinavian SLE | Cases (536) | 309 (57.6%) | 200 (37.3%) | 27 (5.0%) | 11.7874 | 0.0028 | GG: 2.12 (1.29-3.47) GA: 1.59 (0.96-2.63) | 818 (76.3%) | 254 (23.7%) | 7.27E-04 | 1.39 (1.14-1.68) |
| | | Controls (565) | 276 (48.8%) | 238 (42.1%) | 51 (9.0%) | | | | 790 (69.9%) | 340 (30.1%) | | |
| | Argentina SLE | Cases (255) | 164 (64.3%) | 75 (29.4%) | 16 (6.3%) | 3.8013 | 0.1495 | GG: 1.41 (0.73-2.72) GA: 1.01 (0.51-2.00) | 403 (79%) | 107 (21%) | 0.0564 | 1.31 (0.98-1.74) |
| | | Controls (337) | 190 (56.4%) | 121 (35.9%) | 26 (7.7%) | | | | 499 (74.3%) | 173 (25.7%) | | |
| | Germany SLE | Cases (312) | 181 (58.0%) | 118 (37.8%) | 13 (4.2%) | 11.8503 | 0.0027 | GG: 2.60 (1.32-5.14) GA: 1.73 (0.87-3.44) | 480 (76.9%) | 144 (23.1%) | 8.13E-04 | 1.52 (1.18-1.95) |
| | | Controls (368) | 166 (46.1%) | 163 (45.3%) | 31 (8.6%) | | | | 495 (68.8%) | 225 (31.2%) | | |
| | Italy SLE | Cases (279) | 166 (59.5%) | 100 (35.8%) | 13 (4.7%) | 7.5139 | 0.0234 | GG: 2.49 (1.22-5.09) GA: 1.88 (0.91-3.91) | 432 (77.4%) | 126 (22.6%) | 0.0078 | 1.46 (1.09-1.94) |
| | | Controls (245) | 123 (50.2%) | 98 (40.0%) | 24 (9.8) | | | | 344 (70.2%) | 146 (29.8%) | | |
| | Spain SLE | Cases (702) | 414 (59.0%) | 243 (34.6%) | 45 (6.4%) | 11.3579 | 0.0034 | GG: 1.26 (0.77-2.06) GA: 0.82 (0.50-1.35) | 1071 (76.3%) | 333 (23.7%) | 0.0065 | 1.30 (1.07-1.58) |
| | | Controls (446) | 219 (49.1%) | 197 (44.2%) | 30 (6.7%) | | | | 635 (71.2%) | 257 (28.8%) | | |
| | Pooled | Cases (2003) | 1187 (59.3%) | 706 (35.2%) | 110 (5.5%) | | | | 3080 (76.9%) | 926 (23.1%) | 3.74E-10 | 1.38 (1.25-1.53) c |
| | | Controls (1968) | 974 (49.9%) | 817 (41.8%) | 162 (8.3%) | | | | 2763 (70.8%) | 1141 (29.2%) | | |

| | Population | | TT | CT | CC | Chi square | P-Value | Odds ratio (CI) | Allele T | Allele C | P-Value | Odds ratio (CI) |
|---|---|---|---|---|---|---|---|---|---|---|---|---|
| rs17266594 | Scandinavian SLE | Cases (511) | 296 (57.9%) | 189 (37.0%) | 26 (5.1) | 9.4399 | 0.0089 | TT: 2.17 (1.28-3.66) CT: 1.75 (1.03-2.99) | 781 (76.4%) | 241 (23.6%) | 0.0036 | 1.36 (1.10-1.68) |
| | | Controls (416) | 210 (50.5%) | 166 (39.9%) | 40 (9.6%) | | | | 586 (70.4%) | 246 (29.6%) | | |
| | Argentina SLE | Cases (274) | 188 (68.6%) | 77 (28.1%) | 9 (3.3%) | 14.1697 | 8.38E-04 | TT: 3.26 (1.51-7.06) CT: 2.07 (0.93-4.59) | 453 (82.7%) | 95 (17.3%) | 1.06E-04 | 1.73 (1.30-2.31) |
| | | Controls (346) | 192 (55.5%) | 124 (35.8%) | 30 (8.7%) | | | | 508 (73.4%) | 184 (26.6%) | | |
| | Germany SLE | Cases (241) | 132 (54.8%) | 98 (40.7%) | 11 (4.6%) | 7.7164 | 0.0211 | TT: 2.46 (1.19-5.09) CT: 1.81 (0.87-3.76) | 362 (75.1%) | 120 (24.9%) | 0.0080 | 1.43 (1.09-1.87) |
| | | Controls (335) | 151 (45.1%) | 153 (45.7%) | 31 (9.3%) | | | | 455 (67.9%) | 215 (32.1%) | | |
| | Italy SLE | Cases (231) | 130 (56.3%) | 87 (37.7%) | 14 (6.1%) | 10.1706 | 0.0062 | TT: 2.42 (1.19-4.93) CT: 1.45 (0.71-2.97) | 347 (75.1%) | 115 (24.9%) | 0.0016 | 1.59 (1.18-2.14) |
| | | Controls (219) | 92 (42.0%) | 103 (47.0%) | 24 (11.0%) | | | | 287 (65.5%) | 161 (34.5%) | | |
| | Spain SLE | Cases (678) | 404 (59.6%) | 231 (34.1%) | 43 (6.3%) | 14.8617 | 5.93E-04 | TT: 1.04 (0.62-1.76) CT: 0.65 (0.38-1.09) | 1039 (76.6%) | 317 (23.4%) | 0.010 | 1.29 (1.06-1.56) |
| | | Controls (458) | 225 (49.1%) | 208 (45.4%) | 25 (5.5%) | | | | 658 (71.8%) | 258 (28.2%) | | |
| | Pooled | Cases (1856) | 1102 (59.4%) | 655 (35.3%) | 99 (5.3%) | | | | 2859 (77.0%) | 853 (23.0%) | 4.74E-11 | 1.42 (1.28-1.58) c |
| | | Controls (1774) | 870 (49.0%) | 754 (42.5%) | 150 (8.5%) | | | | 2494 (70.3%) | 1054 (29.7%) | | |

| | Population | | TG/TG | TG/other | other/other | Chi square | P-Value | | TG | other | P-Value | Odds ratio (CI) |
|---|---|---|---|---|---|---|---|---|---|---|---|---|
| Haplotype | Scandinavian SLE | Cases (509) | 293 (57.6%) | 190 (37.3%) | 26 (5.1%) | 4.6600 | 0.0973 | | 776 (76.3%) | 242 (23.8%) | 0.22738 | 1.14 (0.91-1.43) |
| | | Controls (365) | 205 (56.2%) | 128 (35.1%) | 32 (8.8%) | | | | 538 (73.8%) | 192 (26.4%) | | |
| | Argentina SLE | Cases (260) | 187 (71.9%) | 55 (25.0%) | 8 (3.1%) | 11.8483 | 0.0027 | | 439 (84.4%) | 81 (15.6%) | 0.00032 | 1.72 (1.27-2.36) |
| | | Controls (317) | 189 (59.6%) | 103 (32.5%) | 25 (7.9%) | | | | 481 (75.9%) | 153 (24.1%) | | |
| | Germany SLE | Cases (237) | 131 (55.3%) | 94 (39.7%) | 12 (5.1%) | 6.6099 | 0.0367 | | 356 (75.1%) | 118 (24.9%) | 0.01228 | 1.40 (1.07-1.85) |
| | | Controls (331) | 151 (45.6%) | 150 (45.3%) | 30 (9.1%) | | | | 452 (68.3%) | 210 (31.7%) | | |
| | Italy SLE | Cases (230) | 130 (56.5%) | 87 (37.8%) | 13 (6.7%) | 9.4922 | 0.0067 | | 347 (75.4%) | 113 (24.6%) | 0.00225 | 1.57 (1.16-2.13) |
| | | Controls (214) | 92 (43.0%) | 99 (46.3%) | 23 (10.7%) | | | | 283 (66.1%) | 145 (33.9%) | | |
| | Spain SLE | Cases (589) | 324 (55.0%) | 217 (36.8%) | 48 (8.1%) | 5.4954 | 0.0641 | | 865 (73.4%) | 313 (26.6%) | 0.43109 | 1.09 (0.88-1.34) |
| | | Controls (374) | 185 (49.7%) | 165 (44.1%) | 23 (6.1%) | | | | 537 (71.8%) | 211 (28.2%) | | |
| | Pooled | Cases (1825) | 1065 (58.4%) | 653 (35.8%) | 107 (5.9%) | | | | 2783 (76.2%) | 867 (23.8%) | 4.75E-06 | 1.30 (1.16-1.45) |
| | | Controls (1601) | 823 (51.4%) | 545 (40.3%) | 133 (6.3%) | | | | 2291 (71.5%) | 911 (28.5%) | | | a Genotypic odds ratio calculated using homozygosity for the protective allele as reference with OR = 1
b Mantel-Haenzel Chi square using fixed effects
c Using the Robins, Breslow and Greenland method

SUPPLEMENTARY TABLE 2

| SNP rs number | MB Build 36 | Location in BANK1 |
|---|---|---|
| rs7675129 | 102894046 | intergenic |
| rs11726012 | 102925041 | promoter |
| rs11097755 | 102928331 | 5'UTR |
| rs4522865 | 102934911 | intronic |
| rs4496585 | 102937309 | intronic |
| rs4572885 | 102954536 | intronic |
| rs10516487 | 102970099 | exon coding (NS)* |
| rs10516486 | 102970299 | exon 2 (synonymous) |
| rs17200824 | 102971612 | intronic |
| rs6849308 | 102995106 | intronic |
| rs10516482 | 102999193 | intronic |
| rs10516483 | 103010928 | intronic |
| rs10516484 | 103011108 | intronic |
| rs4493533 | 103039707 | intronic |
| rs3733197 | 103058310 | exon coding NS |
| rs2631271 | 103133419 | intronic |
| rs2850390 | 103163019 | intronic |
| rs2631265 | 103164099 | intronic |
| rs2631267 | 103167495 | intronic |
| rs2631268 | 103167753 | intronic |
| rs10516491 | 103171889 | intronic |
| rs1872701 | 103172704 | intronic |
| rs2850393 | 103174239 | intronic |
| rs2850396 | 103187471 | intronic |
| rs10516490 | 103193084 | intronic |
| rs10516489 | 103193382 | intronic |
| rs10516488 | 103196800 | intronic |
| rs1395306 | 103204873 | intronic |

*NS: non-synonymous substitution

SUPPLEMENTARY TABLE 3

Genotypic and Allelic Association of rs3733197 in five sets of SLE cases and controls and joint analysis with Mantel-Haenzel test.

| Population | | GG | GA | AA | Chi square | P-Value | Odds ratio (CI) a |
|---|---|---|---|---|---|---|---|
| Scandinavian SLE | Cases (419) | 167 (39.9%) | 192 (45.8%) | 60 (14.3%) | 1.2365 | 0.5389 | GG: 1.04 (0.69-1.58) |
| | Controls (444) | 163 (36.7%) | 220 (49.6%) | 61 (13.7%) | | | GA: 0.89 (0.59-1.33) |
| Argentina SLE | Cases (287) | 177 (61.7%) | 97 (33.8%) | 13 (4.5%) | 9.6496 | 0.0080 | GG: 2.36 (1.20-4.66) |
| | Controls (363) | 184 (50.7%) | 147 (40.5%) | 32 (8.8%) | | | GA: 1.62 (0.81-3.25) |
| Germany SLE | Cases (272) | 128 (47.1%) | 112 (41.2%) | 32 (11.8%) | 4.1431 | 0.1260 | GG: 1.65 (1.01-2.69) |
| | Controls (362) | 148 (40.9%) | 153 (42.3%) | 61 (16.9%) | | | GA: 1.40 (0.85-2.28) |
| Italy SLE | Cases (253) | 131 (51.8%) | 102 (40.3%) | 20 (7.9%) | 8.2595 | 0.0161 | GG: 1.74 (0.92-3.29) |
| | Controls (251) | 98 (39.0%) | 127 (50.6%) | 26 (10.4%) | | | GA: 1.04 (0.55-1.98) |
| Spain SLE | Cases (588) | 307 (52.2%) | 234 (39.8%) | 47 (8.0%) | 3.4580 | 0.1775 | GG: 1.14 (0.72-1.82) |
| | Controls (455) | 212 (46.6%) | 206 (45.3%) | 37 (8.1%) | | | GA: 0.89 (0.56-1.43) |
| Pooled | Cases (1819) | 910 (50.0%) | 737 (40.5%) | 172 (9.5%) | | | |
| | Controls (1875) | 805 (42.9%) | 853 (45.5%) | 217 (11.6%) | | | |

| Population | | Allele G | Allele A | Chi square | P-Value | Odds ratio (CI) |
|---|---|---|---|---|---|---|
| Scandinavian SLE | Cases (419) | 526 (62.8%) | 312 (37.2%) | 0.301 | 0.5832 | 1.06 (0.87-1.29) |
| | Controls (444) | 546 (61.5%) | 342 (38.5%) | | | |
| Argentina SLE | Cases (287) | 451 (78.6%) | 123 (21.4%) | 9.787 | 0.0018 | 1.15 (0.95-1.40) |
| | Controls (363) | 515 (70.9%) | 211 (29.1%) | | | |
| Germany SLE | Cases (272) | 368 (67.6%) | 176 (32.4%) | 4.297 | 0.0382 | 1.28 (1.00-1.63) |
| | Controls (362) | 449 (62.0%) | 275 (38.0%) | | | |
| Italy SLE | Cases (253) | 364 (71.9%) | 142 (28.1%) | 6.696 | 0.0097 | 1.42 (1.08-1.87) |
| | Controls (251) | 323 (64.3%) | 179 (35.7%) | | | |
| Spain SLE | Cases (588) | 977 (72.1%) | 379 (27.9%) | 2.099 | 0.1474 | 1.50 (1.15-1.96) |
| | Controls (455) | 630 (69.2%) | 280 (30.8%) | | | |
| Pooled | Cases (1819) | 2686 (70.4%) | 1132 (29.6%) | 16.5763 | 4.67E−05 | 1.23 (1.11-1.36) |
| | Controls (1875) | 2463 (65.7%) | 1287 (34.3%) | | | |

SUPPLEMENTARY TABLE 4

Primer sequences

| Gene/gene fragment/isoform | Forward | SEQ ID NO | Reverse | SEQ ID NO |
|---|---|---|---|---|
| hBANK cDNA amplification | CACCTCAACCGCCACAATGCTGCCAGCA | 7 | ATAATAACCTTCTTTAATGATCTTTCTTGC | 8 |
| Total BANK1 qRT-PCR | AGAGGAAACTACACCTTACATAGCTC | 9 | GATGAGTTCTTCCTGACCATCAG | 10 |
| Total full-length isoforms | TCAAAGCAGATGGGAGATCTCAAC | 11 | | |
| Delta2 isoform | CAGCGCCCCCAGATTCTGAAG | 12 | | |
| Exon1A full-length isoform | CAGCGCCCCCAGGAAATACA | 13 | | |

SUPPLEMENTARY TABLE 4-continued

Primer sequences

| Gene/gene fragment/isoform | Forward | SEQ ID NO | | SEQ ID NO |
|---|---|---|---|---|
| Alternative exon1 full-length isoform | GCCTATTCTTTGTTTTGG AAATACA | 14 | | |
| | | | Common reverse primer for all isoforms for qRT-PCR | |
| | | | CACATGGAATTTCAGTGGG AAGCAC | 15 |
| | | | Common reverse primer for gel-analysis | |
| | | | ATCACAGTAGACATTGACA TGGAC | 16 |

For Genomic Sequencing:

| Gene/gene fragment/isoform | Forward | SEQ ID NO | Reverse | SEQ ID NO |
|---|---|---|---|---|
| promoter, exon 1A and 5'-part of intron 1 | TTGGAGAGGGTATTTA GAGCCATA | 17 | AAGCAGGGCTACCAATT CACCAG | 18 |
| Alternative exon1B | CTATGATACTGGAAAT ACTGTCAGT | 19 | AGCATATGACCAGCTGA TCAG | 20 |
| Exon2 | TTGATTTACTATGAAA ATATCAAGC | 21 | TTACATAAGAAACCAGC TTCCAG | 22 |
| mouse BANK1 Cdna | ACCTCCCGCAATGCT TCCTGT | 23 | ACATGGAATTTCCCCAG GAAGCAC | 24 |

REFERENCE LIST

1. Sherer, Y., Gorstein, A., Fritzler, M. J. & Shoenfeld, Y. (2004) Semin Arthritis Rheum 34, 501-37.
2. Former K, L. M., Guedj M, Dauvillier J and Wojcik J. Hum Hered, In Press.
3. Yokoyama, K., Su Ih, I. H., Tezuka, T., Yasuda, T., Mikoshiba, K., Tarakhovsky, A. & Yamamoto, T. (2002) Embo J 21, 83-92.
4. Aiba, Y., Yamazaki, T., Okada, T., Gotch, K., Sanjo, H., Ogata, M. & Kurosaki, T. (2006) Immunity 24, 259-68.
5. Burge, C. B., Tuschl, T. & Sharp, P. A (1999), ed. Gesteland, R. F., Cech, T. R. & Atkins, J. F (Cold Spring Harbor Laboratory Press, Cold Spring Harbor, N.Y.), pp. 525-560.
6. Jordan, M. S., Singer, A. L. & Koretzky, G. A. (2003) Nat Immunol 4, 110-6.
7. Kurosaki, T. (2002) Nat Rev Immunol 2, 354-63.
8. Okada, T., Maeda, A., Iwamatsu, A., Gotoh, K. & Kurosaki, T. (2000) Immunity 13, 817-27.
9. Patterson, R. L., Boehning, D. & Snyder, S. H. (2004) Annu Rev Biochem 73, 437-65.
10. Mohler, P. J., Schott, J. J., Gramolini, A. O., Dilly, K. W., Guatimosim, S., duBell, W. H., Song, L. S., Haurogne, K., Kyndt, F., Ali, M. E., Rogers, T. B., Lederer, W. J., Escande, D., Le Marec, H. & Bennett, V. (2003) Nature 421, 634-9.
11. Blom, N., Gammeltoft, S. & Brunak, S. (1999) J Mol Biol 294, 1351-62.
12. Anolik, J., Sanz, I. & Looney, R. J. (2003) Curr Rheumatol Rep 5, 350-6.
13. Liossis, S. N., Kovacs, B., Dennis, G., Kammer, G. M. & Tsokos, G. C. (1996) J Clin Invest 98, 2549-57.
14. Huck, S., Le Corre, R., Youinou, P. & Zouali, M. (2001) Autoimmunity 33, 213-24.
15. Liossis, S. N., Solomou, E. E., Dimopoulos, M. A., Panayiotidis, P., Mavrikakis, M. M. & Sfikakis, P. P. (2001) J Investig Med 49, 157-65.
16. Hibbs, M. L., Harder, K. W., Armes, J., Kountouri, N., Quilici, C., Casagranda, F., Dunn, A. R. & Tarlinton, D. M. (2002) J Exp Med 196, 1593-604.
17. Flores-Borja, F., Kabouridis, P. S., Jury, E. C., Isenberg, D. A. & Mageed, R. A. (2005) Arthritis Rheum 52, 3955-65.
18. Cornall, R. J., Oyster, J. G., Hibbs, M. L., Dunn, A. R., Otipoby, K. L., Clark, E. A. & Goodnow, C. C. (1998) Immunity 8, 497-508.
19. Kozyrev, S. V., Lewén, S., Ling a Reddy, M. V. P., Pons-Estel, B. A., The Argentine Collaborative Group, Witte, T., The German Collaborative Group, Junker, P., Laustrup, H., Gutiérrez, C., Suárez, A., González-Escribano, M. F., Martin, J., The Spanish Collaborative Group and Alarcón-Riquelme, M. E. (2007) Arthritis and Rheumatism 56, 1234-41.
20. Tan, E. M., Cohen, A. S., Fries, J. F., Masi, A. T., McShane, D. J., Rothfield, N. F., Schaller, J. G., Talal, N. & Winchester, R. J. (1982) Arthritis Rheum 25, 1271-7.
21. Guedj, M., Wojcik, J., Della-Chiesa, E., Nuel, G. & Forner, K. (2006) Hum Hered 61, 210-21.
22. Stephens, M. & Donnelly, P. (2003) Am J Hum Genet 73, 1162-9.

23. Stephens, M., Smith, N. J. & Donnelly, P. (2001) *Am J Hum Genet* 68, 978-89.
24. Dudbridge, F. (2003) *Genet Epidemiol* 25, 115-21.
25. Freeman, W. M. and S. E. Hemby (2004). "Proteomics for protein expression profiling in neuroscience." *Neurochem Res* 29(6): 1065-81.
26. Gut, I. G. (2004). "DNA analysis by MALDI-TOF mass spectrometry." *Hum Mutat* 23(5): 437-41.
27. Shi, M. M. (2001). "Enabling large-scale pharmacogenetic studies by high-throughput mutation detection and genotyping technologies." *Clin Chem* 47(2): 164-72.
28. Zhu, H. and M. Snyder (2003). "Protein chip technology." *Curr Opin Chem Biol* 7(1): 55-63.

The invention claimed is:

1. An isolated nucleic acid molecule comprising the sequence of B-cell scaffold protein with ankyrin repeats (BANK1) lacking exon 2.

2. The isolated nucleic acid molecule according to claim 1, wherein the sequence is obtained from a human, chimpanzee, or mouse.

3. The isolated nucleic acid molecule according to claim 1, said nucleic acid molecule comprising SEQ ID NO: 1, 3, or 5, or the complement of said nucleic acid sequence.

4. A vector comprising a nucleic acid molecule according to claim 1.

5. The vector according to claim 4, wherein said nucleic acid molecule is operatively linked to at least one expression control sequence allowing expression in prokaryotic or eukaryotic host cells of the encoded polypeptide.

6. The vector according to claim 4, wherein said nucleic acid molecule comprises SEQ ID NO: 1.

7. The vector according to claim 4, wherein said nucleic acid molecule comprises SEQ ID NO: 3.

8. The vector according to claim 4, wherein said nucleic acid molecule comprises SEQ ID NO: 5.

9. An isolated host cell transformed with a nucleic acid molecule according to claim 1.

10. The host cell according to claim 9, wherein said host cell is transformed with a vector comprising the sequence of BANK1 lacking exon 2.

11. The host cell according to claim 10, wherein said vector comprises SEQ ID NO: 1.

12. The host cell according to claim 10, wherein said vector comprises SEQ ID NO: 3.

13. The host cell according to claim 10, wherein said vector comprises SEQ ID NO: 5.

14. A method for making a polypeptide comprising culturing a cell according to claim 9 under conditions in which the nucleic acid is expressed, and recovering the polypeptide encoded by said nucleic acid from the culture.

15. The host cell according to claim 9, wherein said nucleic acid molecule comprises SEQ ID NO: 1.

16. The host cell according to claim 9, wherein said nucleic acid molecule comprises SEQ ID NO: 3.

17. The host cell according to claim 9, wherein said nucleic acid molecule comprises SEQ ID NO: 5.

18. The isolated nucleic acid according to claim 1, wherein the nucleic acid is a mRNA, cRNA or cDNA.

19. An insolated polypeptide encoded by a nucleic acid molecule comprising the sequence of B-cell scaffold protein with ankyrin repeats (BANK1) lacking exon 2.

* * * * *

UNITED STATES PATENT AND TRADEMARK OFFICE
CERTIFICATE OF CORRECTION

| | | |
|---|---|---|
| PATENT NO. | : 8,105,816 B2 | Page 1 of 1 |
| APPLICATION NO. | : 12/738418 | |
| DATED | : January 31, 2012 | |
| INVENTOR(S) | : Hadi Abderrahim and Sergei V. Kozyrev | |

It is certified that error appears in the above-identified patent and that said Letters Patent is hereby corrected as shown below:

Column 4,
Line 31, "tyrosin" should read --thymine--.
Line 47, "tyrosine" should read --thymine--.

Column 6,
Line 28, "may be most reliably be used" should read --may most reliably be used--.

Column 10,
Line 36, "by Former," should read --by Forner,--.

Column 14, Table 2,
Section Haplotype, Row Italy SLE, Column P-Value, "0.0067" should read --0.0087--.

Column 17,
Line 42, "2. Former" should read --2. Forner--.

Column 18,
Line 51, "Oyster" should read --Cyster--.
Line 54, "Ling a Reddy" should read --Linga Reddy--.

Signed and Sealed this
Nineteenth Day of June, 2012

David J. Kappos
*Director of the United States Patent and Trademark Office*